US008604279B2

(12) United States Patent
Brede et al.

(10) Patent No.: US 8,604,279 B2
(45) Date of Patent: Dec. 10, 2013

(54) GLYPHOSATE TOLERANT PERENNIAL RYEGRASS NAMED 'JS501'

(75) Inventors: Andrew Douglas Brede, Verdale, WA (US); Susan H. Samudio, Spokane, WA (US); Caius Rommens, Boise, ID (US); Jingsong Ye, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 266 days.

(21) Appl. No.: 12/906,738

(22) Filed: Oct. 18, 2010

(65) Prior Publication Data

US 2011/0191876 A1 Aug. 4, 2011

Related U.S. Application Data

(60) Provisional application No. 61/252,930, filed on Oct. 19, 2009.

(51) Int. Cl.
*A01H 1/00* (2006.01)
*A01H 5/00* (2006.01)
*A01H 5/10* (2006.01)

(52) U.S. Cl.
USPC ............ 800/300; 435/410; 800/266; 800/320

(58) Field of Classification Search
None
See application file for complete search history.

(56) References Cited

U.S. PATENT DOCUMENTS

| | | | |
|---|---|---|---|
| 4,405,531 A | 9/1983 | Franz | |
| 4,769,061 A | 9/1988 | Comai | |
| 4,940,835 A | 7/1990 | Shah et al. | |
| 4,975,374 A | 12/1990 | Goodman et al. | |
| 5,118,338 A | 6/1992 | Moller | |
| 5,196,044 A | 3/1993 | Caulder et al. | |
| 5,639,711 A | 6/1997 | Kassebaum et al. | |
| 5,652,197 A | 7/1997 | Claude et al. | |
| 5,679,621 A | 10/1997 | Magin et al. | |
| 5,750,468 A | 5/1998 | Wright et al. | |
| 5,959,185 A | 9/1999 | Streit et al. | |
| 5,973,234 A | 10/1999 | Mueller et al. | |
| 5,977,445 A | 11/1999 | Soper et al. | |
| 6,025,545 A | 2/2000 | Lundquist et al. | |
| 7,465,857 B1 | 12/2008 | van't Klooster | |
| 7,906,709 B2 * | 3/2011 | Penner et al. ............... | 800/300 |
| 2003/0221213 A1 | 11/2003 | Rommens et al. | |
| 2004/0107455 A1 | 6/2004 | Rommens et al. | |

FOREIGN PATENT DOCUMENTS

| | | |
|---|---|---|
| EP | 0 242 246 | 10/1987 |
| EP | 0 333 033 | 9/1989 |
| WO | WO 03/069980 | 8/2003 |
| WO | WO 2005/004585 | 1/2005 |

OTHER PUBLICATIONS

Ansari et al 1989, Biochemistry 28: 8665-8670.*
Degreef, W. et al. "Evaluation of Herbicide Resistance in Transgenic Crops Under Field Conditions." Bio/Technology vol. 7, 1989, pp. 61-64.
Marshall, L.C. et al. "Allelic mutations in acetyl-coenzyme A carboxylase confer herbicide tolerance in maize." Theoretical and Applied Genetics vol. 83, 1992, pp. 435-442.
Comai, L. et al. "Expression in plants of a mutant aroA gene from *Salmonella typhimurium* confers tolerance to glyphosate." Nature vol. 317 No. 24, 1985, pp. 741-744.
Gordon-Kamm, W. et al. "Transformation of Maize Cells and Regeneration of Fertile Transgenic Plants." The Plant Cell vol. 2, Jul. 1990, pp. 603-618.
Stalker, D. et al. "Herbicide Resistance in Transgenic Plants Expressing a Bacterial Detoxification Gene." Science vol. 242, 1988, pp. 419-423.
Altpeter, F. et al. "Generation of large numbers of independently transformed fertile perennial ryegrass (*Lolium perenne* L.) plants of forage- and turf-type cultivars." Molecular Breeding vol. 6, 2000, pp. 519-528.
Bradley, D.E. et al. "Effects of Cultivar, Explant Treatment, and Medium Supplements on Callus Induction and Plantlet Regeneration in Perennial Ryegrass." International Turfgrass Society Research Journal vol. 9, 2001, pp. 152-156.
Stalker, D. et al. "A Single Amino Acid Substitution in the Enzyme 5-Enolpyruvylshikimate-3-phosphate Synthase Confers Resistance to the Herbicide Glyphosate" Journal of Biological Chemistry vol. 260, No. 8, 1985, pp. 4724-4728.
Huynh, Q. et al. "Site-directed Mutagenesis of Petunia hybrida 5-Enolpyruvylshikimate-3-phosphate Synthase: Lys-23 is Essential for Substrate Binding." Journal of Biological Chemistry vol. 263, No. 24, 1988, pp. 11636-11639.
Jain et al. "Transgenic strategies for genetic improvement of Basmati rice." Indian Journal of Experimental Biology vol. 38, Jan. 2000, pp. 6-17.

\* cited by examiner

*Primary Examiner* — David H Kruse
(74) *Attorney, Agent, or Firm* — Foley & Lardner LLP

(57) ABSTRACT

The present invention relates to a new, distinct and stable variety of glyphosate tolerant perennial ryegrass, botanically known as *Lolium perenne* L. of the Poaceae family, and hereinafter referred to by the variety denomination 'JS501'. The present invention relates to glyphosate tolerant perennial ryegrass 'JS501' plants, as well as, progeny or hybrid plants, seed, plant parts, harvested products, tissue cultures of regenerable cells, and protoplasts obtained from the glyphosate tolerant perennial ryegrass plants or plant tissues of 'JS501', and containing morphological and physiological characteristics of 'JS501'. The present invention further relates to methods of producing non-transgenic and transgenic glyphosate tolerant grass plants and plant tissues from conventional breeding techniques and molecular techniques, wherein the produced glyphosate tolerant grass plants and plant tissues comprise the isolated perennial ryegrass 5-enolpyruvylshikimate 3-phosphate synthase (EPSPS) polypeptide of 'JS501'.

10 Claims, 2 Drawing Sheets

(2 of 2 Drawing Sheet(s) Filed in Color)

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cagcccatca aggagatctc cggc                                           24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctagttcttc acgaaggtgc ttagc                                          25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggcgccgtg cagctgcccg gctc                                           24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aggtgcttag cacgtcaaag ta                                             22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagcgttttg gcgtgacagc agagc                                          25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued

```
catgtaacct tcgctcccat c                                              21
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gacagaagta caagtcccct gga                                            23
```

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ctccagtgat tgcagcacca gc                                             22
```

<210> SEQ ID NO 9
<211> LENGTH: 1279
<212> TYPE: DNA
<213> ORGANISM: Lolium perenne

<400> SEQUENCE: 9

```
ggcgccgtgc agctgcccgg ctccaagtcg ctctccaacc ggatcctcct cctctccgcc    60
ttgtccgagg gaacaacggt ggtggataac ctgttgaaca gtgaggatgt ccactacatg   120
ctcgaggccc tggacgcgct cggcctctcc gtggaagcag acaaagttgc aaaaagagct   180
gtagtcgtcg gctgcggcgg caggttcccg attgaaaagg atgccaagga ggaagtaaag   240
ctcttcctgg ggaacgctgg aactgcgatg cggccattga cggcggcggt agtagctgct   300
ggcggaaaag caacttatgt tcttgatgga gtaccaagaa tgagggagcg acctatcggt   360
gacttagttg tcggtttgaa acaactaggt gcgaatgttg attgtttcct cggcaccgac   420
tgcccacctg ttcgtatcaa cggcattgga gggctacctg gtggcaaggt taagctatct   480
ggttccatca gcagccagta cttgagttcc ttgctgatgg ctgctccttt ggctcttggg   540
gatgttgaga ttgaaatcat tgataaacta atctctgttc cttatgttga aatgacattg   600
agattgatgg agcgttttgg cgtgacagca gagcattctg atagctggga cagattctac   660
attaaaggag gacagaagta caagtcccct ggaaatgcct atgtcgaagg tgatgcctca   720
agtgcgagct atttcttggc tggcgctgca atcactggag gaactgtgac tgtccaaggt   780
tgcggcacca ccagtttgca gggtgatgtg aaatttgctg aggtactaga aatgatggga   840
gcgaaagtta catggaccga cactagtgta actgttactg gtccaccacg tcagcccttt   900
ggaaggaaac acctaaaagc tgttgatgtc aacatgaaca aaatgcctga tgttgccatg   960
actcttgccg ttgttgccct tttcgccgat ggtccaactg ctatcagaga tgttgcctct  1020
tggagagtga aggaaaccga gagaatggtg gcaatccgga cggaactaac aaagctggga  1080
gcaacggtag aggaaggccc agactactgc attatcacac caccagagaa gctgaacgtc  1140
acggcaatcg acacctacga tgaccaccgg atggcgatgg ccttctccct cgccgcctgc  1200
gctgaggtgc ctgtcacgat cagggaccct gggtgcaccc gcaagacctt ccccaactac  1260
tttgacgtgc taagcacct                                               1279
```

<210> SEQ ID NO 10
<211> LENGTH: 1279
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
ggcgccgtgc agctgcccgg ctccgagtcg ctctccaacc ggatcctcct cctctccgcc      60
ttgtccgagg gaacaacggt ggtggataac ctgttgaaca gtgaggatgt ccactacatg     120
ctcgaggccc tggacgcgct cggcctctcc gtggaagcag acaaagttgc aaaaagagct     180
gtagtcgtcg gctgcggcgg caggttcccg attgaaaagg atgccaagga ggaagtaaag     240
ctcttcctgg ggaacgctgg aactgcgatg cggtcattga cggcggcggt agtagctgct     300
ggcggaaaag caacttatgt tcttgatgga gtaccaagaa tgagggagcg acctatcggt     360
gacttagttg tcggtttgaa acaactaggt gcgaatgttg attgtttcct cggcaccgac     420
tgcccacctg ttcgtatcaa cggcattgga gggctacctg gtggcaaggt taagctatct     480
ggttccatca gcagccagta cttgagttcc ttgctgatgg ctgctccttt ggctcttggg     540
gatgttgaga ttgaaatcat tgataaacta atctctgttc cttatgttga atgacattg     600
agattgatgg agcgttttgg cgtgacagca gagcattctg atagctggga cagattctac     660
attaaaggag acagaagta caagtcccct ggaaatgcct atgtcgaagg tgatgcctca     720
agtgcgagct atttcttggc tggcgctgca atcactggag gaactgtgac tgtccaaggt     780
tgcggcacca ccagtttgca gggtgatgtg aaatttgctg aggtactaga aatgatggga     840
gcgaaagtta catggaccga cactagtgta actgttactg gtccaccacg tcagcccttt     900
ggaaggaaac acctaaaagc tgttgatgtc aacatgaaca aaatgcctga tgttgccatg     960
actcttgccg ttgttgccct tttcgccgat ggtccaactg ctatcagaga tgttgcctct    1020
tggagagtga aggaaaccga gagaatggtg gcaatccgga cggaactaac aaagctggga    1080
gcaacggtag aggaaggccc agactactgc attatcacac caccagagaa gctgaacgtc    1140
acggcaatcg acacctacga tgaccaccgg atggcgatgg ccttctccct cgccgcctgc    1200
gctgaggtgc ctgtcacgat cagggacccct gggtgcaccc gcaagacctt ccccaactac    1260
tttgacgtgc taagcacct                                                  1279
```

<210> SEQ ID NO 11
<211> LENGTH: 426
<212> TYPE: PRT
<213> ORGANISM: Escherichia coli

<400> SEQUENCE: 11

```
Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95
```

Thr Ala Met Arg Pro Leu Ala Ala Ala Leu Cys Leu Gly Ser Asn Asp
                100                 105                 110

Ile Val Leu Thr Gly Glu Pro Arg Met Lys Glu Arg Pro Ile Gly His
            115                 120                 125

Leu Val Asp Ala Leu Arg Leu Gly Gly Ala Lys Ile Thr Tyr Leu Glu
        130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Gln Phe Leu Thr Ala Leu
                165                 170                 175

Leu Met Thr Ala Pro Leu Ala Pro Glu Asp Thr Val Ile Arg Ile Lys
                180                 185                 190

Gly Asp Leu Val Ser Lys Pro Tyr Ile Asp Ile Thr Leu Asn Leu Met
            195                 200                 205

Lys Thr Phe Gly Val Glu Ile Glu Asn Gln His Tyr Gln Gln Phe Val
        210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
            290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala
                420                 425

<210> SEQ ID NO 12
<211> LENGTH: 269
<212> TYPE: PRT
<213> ORGANISM: Lolium perenne

<400> SEQUENCE: 12

Gly Ala Val Gln Leu Pro Gly Ser Lys Ser Leu Ser Asn Arg Ile Leu
1               5                   10                  15

Leu Leu Ser Ala Leu Ser Glu Gly Thr Thr Val Val Asp Asn Leu Leu
            20                  25                  30

Asn Ser Glu Asp Val His Tyr Met Leu Glu Ala Leu Asp Ala Leu Gly
        35                  40                  45

Leu Ser Val Glu Ala Asp Lys Val Ala Arg Ala Val Val Gly
        50                  55                  60

Cys Gly Gly Arg Phe Pro Ile Glu Lys Asp Ala Lys Glu Val Lys
65                  70                  75                  80

Leu Phe Leu Gly Asn Ala Gly Thr Ala Met Arg Pro Leu Thr Ala Ala
                85                  90                  95

Val Val Ala Ala Gly Gly Lys Ala Thr Tyr Val Leu Asp Gly Val Pro
                100                 105                 110

Arg Met Arg Glu Arg Pro Ile Gly Asp Leu Val Val Gly Leu Lys Gln
            115                 120                 125

Leu Gly Ala Asn Val Asp Cys Phe Leu Gly Thr Asp Cys Pro Pro Val
        130                 135                 140

Arg Ile Asn Gly Ile Gly Gly Leu Pro Gly Gly Lys Val Lys Leu Ser
145                 150                 155                 160

Gly Ser Ile Ser Ser Gln Tyr Leu Ser Ser Leu Leu Met Ala Ala Pro
                165                 170                 175

Leu Ala Leu Gly Asp Val Glu Ile Glu Ile Ile Asp Lys Leu Ile Ser
            180                 185                 190

Val Pro Tyr Val Glu Met Thr Leu Arg Leu Met Glu Arg Phe Gly Val
        195                 200                 205

Met Ala Glu His Ser Asp Ser Trp Asp Arg Phe Tyr Ile Lys Gly Gly
210                 215                 220

Gln Lys Tyr Lys Ser Pro Gly Asn Ala Tyr Val Glu Gly Asp Ala Ser
225                 230                 235                 240

Ser Ala Ser Tyr Phe Leu Ala Gly Ala Ile Thr Gly Gly Thr Val
                245                 250                 255

Thr Val Gln Val Ala Ala Pro Pro Val Cys Arg Val Met
            260                 265

<210> SEQ ID NO 13
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ala Val Gln Leu Pro Gly Ser Glu Ser Leu Ser Asn Arg Ile Leu
1               5                   10                  15

Leu Leu Ser Ala Leu Ser Glu Gly Thr Thr Val Val Asp Asn Leu Leu
                20                  25                  30

Asn Ser Glu Asp Val His Tyr Met Leu Glu Ala Leu Asp Ala Leu Gly
            35                  40                  45

Leu Ser Val Glu Ala Asp Lys Val Ala Arg Ala Val Val Gly
        50                  55                  60

Cys Gly Gly Arg Phe Pro Ile Glu Lys Asp Ala Lys Glu Val Lys
65                  70                  75                  80

Leu Phe Leu Gly Asn Ala Gly Thr Ala Met Arg Ser Leu Thr Ala Ala
                85                  90                  95

Val Val Ala Ala Gly Gly Lys Ala Thr Tyr Val Leu Asp Gly Val Pro
                100                 105                 110

Arg Met Arg Glu Arg Pro Ile Gly Asp Leu Val Val Gly Leu Lys Gln
            115                 120                 125

Leu Gly Ala Asn Val Asp Cys Phe Leu Gly Thr Asp Cys Pro Pro Val
        130                 135                 140

```
Arg Ile Asn Gly Ile Gly Gly Leu Pro Gly Gly Lys Val Lys Leu Ser
145             150             155             160

Gly Ser Ile Ser Ser Gln Tyr Leu Ser Ser Leu Leu Met Ala Ala Pro
            165             170             175

Leu Ala Leu Gly Asp Val Glu Ile Glu Ile Ile Asp Lys Leu Ile Ser
            180             185             190

Val Pro Tyr Val Glu Met Thr Leu Arg Leu Met Glu Arg Phe Gly Val
        195             200             205

Met Ala Glu His Ser Asp Ser Trp Asp Arg Phe Tyr Ile Lys Gly Gly
    210             215             220

Gln Lys Tyr Lys Ser Pro Gly Asn Ala Tyr Val Glu Gly Asp Ala Ser
225             230             235             240

Ser Ala Ser Tyr Phe Leu Ala Gly Ala Ala Ile Thr Gly Gly Thr Val
            245             250             255

Thr Val Gln Gly Cys Gly Thr Thr Ser Leu Gln Gly Asp Val Lys Phe
            260             265             270

Ala Glu Val Leu Glu Met Met Gly Ala Lys Val Thr
        275             280
```

GLYPHOSATE TOLERANT PERENNIAL RYEGRASS NAMED 'JS501'

PRIORITY CLAIM

The present application claims benefit of U.S. Provisional Application No. 61/252,930, filed Oct. 19, 2009.

SEQUENCE LISTING

The instant application contains a Sequence Listing which has been submitted in ASCII format via EFS-Web and is hereby incorporated by reference in its entirety. Said ASCII copy, created on Nov. 4, 2010, is named 58951368.txt and is 14,425 bytes in size.

FIELD OF THE INVENTION

The present invention relates to glyphosate tolerance in perennial ryegrass (*Lolium perenne* L.). More specifically, the present invention relates to a new, distinct and stable variety of glyphosate tolerant perennial ryegrass, botanically known as *Lolium perenne* L. of the Poaceae family, and hereinafter referred to by the variety denomination 'JS501' (experimental code was 'JR-501' and previously called "Blitz TD"). The present invention relates to glyphosate tolerant perennial ryegrass 'JS501' plants, as well as, progeny or hybrid plants, seed, plant parts, harvested products, tissue cultures of regenerable cells, and protoplasts obtained from the glyphosate tolerant perennial ryegrass plants or plant tissues of 'JS501', and containing morphological and physiological characteristics of 'JS501'. The present invention further relates to methods of producing non-transgenic and transgenic glyphosate tolerant grass plants and plant tissues from conventional breeding techniques and molecular techniques, wherein the produced glyphosate tolerant grass plants and plant tissues comprise the isolated perennial ryegrass 5-enolpyruvylshikimate 3-phosphate synthase (EPSPS) polypeptide of 'JS501'.

BACKGROUND

Perennial ryegrasses are popular for use in turfgrass providing quick germination, fine textured leaves, a dense forming sod, and high disease and insect resistance. Perennial ryegrasses provide an attractive lower maintenance, permanent lawn cover in cooler climates, and can be used for winter overseeding of dormant bermudagrass (*Cynodon dactylon*) in warmer climates to provide green grass through the winter. Perennial ryegrasses have also been used in soil erosion control programs and as forage.

Perennial ryegrass (*Lolium perenne* L.), also called English ryegrass, is a temperate (cool-season) perennial grass that is native to Europe, temperate Asia, and North Africa. It has been widely distributed to other parts of the world, including North and South America, Europe, New Zealand, and Australia. Perennial ryegrass is valued for fast establishment, attractive turf, reduced tillage renovation applications, and use on heavy and waterlogged soils.

Forage-type perennial ryegrasses are important grasses in forage-livestock systems. High palatability and digestibility make this species highly valued for use in dairy and sheep forage systems. As a result, it often is the preferred forage grass in temperate regions of the world.

Use of perennial ryegrass for turf has increased in recent years with selection of more dense and persistent turf types. It is one of the most versatile of all turfgrass species. For turf, perennial ryegrass is used alone (straights), in blends with other perennial ryegrasses, or in mixtures with other grass species on home lawns, athletic fields, golf courses (fairways, roughs and tees), parks, schools, and industrial sites.

Glyphosate (N-(phosphonomethyl)glycine) is the active ingredient in glyphosate herbicides, such as TOUCHDOWN TOTAL® brand herbicide produced by Syngenta Crop Protection, Inc. (Greensboro, N.C.). Typically, glyphosate is formulated as a water-soluble salt such as an ammonium, alkylamine, alkali metal or trimethylsulfonium salt. One of the most common formulations is the isopropylamine salt of glyphosate, which is the form employed in TOUCHDOWN TOTAL® brand herbicide.

Glyphosate is a broad spectrum herbicide that inhibits the enzyme enolpyruvylshikimate-phosphate synthase (EPSPS). It is conventionally applied as an aqueous solution to the foliage of plants, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents disclose various formulations of glyphosate, including U.S. Pat. Nos. 4,405,531; 5,118,338; 5,196,044; 5,639,711; 5,652,197; 5,679,621; and 5,750,468.

A limited amount of success has been reported in finding natural resistance to glyphosate herbicides in plants. This is beneficial in one respect since it indicates that the likelihood of glyphosate resistant populations of weeds arising is low, but it also means that a limited amount of naturally resistant desirable plant species are available. As a result, great care must be taken when applying glyphosate herbicides in the vicinity of desirable plants (such as crops, ornamentals, and grass turf). In particular, glyphosate herbicides are effective against all grass species, and therefore, application of glyphosate herbicides in perennial ryegrasses to control weed growth has resulted in significant turf damage.

New and improved perennial ryegrasses continue to be developed for use as improved turfgrass and for overseeding of athletic fields, home lawns, golf courses (fairways, roughs and tees), parks, schools, and industrial sites, and for use as forage. Research studies have been conducted to identify promising perennial ryegrass varieties and hybrids which express improved traits, such as, turf quality, seedling vigor, weather tolerance, resistance to problematic diseases and pests, as well as, tolerance to applications of glyphosate herbicides.

The glyphosate tolerant perennial ryegrass 'JS501' plants and plant tissues of the present invention were developed for use as improved turfgrass and for winter overseeding of athletic fields, home lawns, golf courses (fairways, roughs and tees), parks, schools, and industrial sites. In addition, the distinctive genetic fingerprint for the glyphosate tolerant perennial ryegrass 'JS501' plant has been analyzed, and the EPSPS polypeptide comprising the amino acid sequence of SEQ ID NO:13, and the polynucleotide having the nucleotide sequence of SEQ ID NO:10 and encoding the EPSPS protein, involved in the regulation of glyphosate tolerance in perennial ryegrass plants and plant tissues have been identified.

SUMMARY

These and other objectives have been achieved in accordance with the present invention which provides 'JS501' as a new, distinct and stable variety of glyphosate tolerant perennial ryegrass, botanically known as *Lolium perenne* L. of the Poaceae family, and hereinafter referred to by the variety denomination 'JS501'.

The present invention relates to glyphosate tolerant perennial ryegrass 'JS501' plants, as well as, progeny or hybrid plants, seed, plant parts, harvested products, tissue cultures of regenerable cells, and protoplasts obtained from the glyphosate tolerant perennial ryegrass plants or plant tissues of 'JS501', and containing morphological and physiological characteristics of 'JS501'.

The present invention relates to a method of producing glyphosate tolerant perennial ryegrass progeny or hybrids comprising the steps of (a) crossing a 'JS501' plant, as either the female or seed parent or male or pollen parent, with a second perennial ryegrass plant, and (b) selecting progeny that are glyphosate tolerant and progeny that are heterozygous for glyphosate tolerance.

The present invention also relates to a method of producing glyphosate tolerant perennial ryegrass progeny or hybrids comprising the steps of (a) crossing a 'JS501' plant, as either the female or seed parent or male or pollen parent, with a second perennial ryegrass plant, (b) harvesting seeds produced from said cross, and (c) producing and selecting glyphosate tolerant progeny and progeny that are heterozygous for glyphosate tolerance from said harvested seeds.

The present invention also relates to a method of producing glyphosate tolerant perennial ryegrass progeny, comprising the steps of (a) selfing 'JS501', and (b) selecting glyphosate tolerant progeny and progeny that are heterozygous for glyphosate tolerance.

The present invention also relates to a method of producing a glyphosate tolerant grass plant, comprising the steps of (a) transforming a non-glyphosate tolerant plant with a polynucleotide sequence coding for EPSPS having the amino acid sequence of SEQ ID NO:13 of 'JS501', and (b) selecting glyphosate tolerant stably transformed plants.

BRIEF DESCRIPTION OF THE DRAWINGS

The patent or application file contains at least one drawing executed in color. Copies of this patent or patent application publication with color drawings will be provided by the Office upon request and payment of the necessary fees.

The accompanying photographs illustrate the overall appearance of the new glyphosate tolerant perennial ryegrass 'JS501' showing the colors as true as is reasonably possible with colored reproductions of this type. Colors in the photographs may differ slightly from the color values cited in the detailed botanical description, which accurately describe the color of the glyphosate tolerant perennial ryegrass 'JS501'.

DETAILED DESCRIPTION

General Definitions and Techniques

Figure 1:
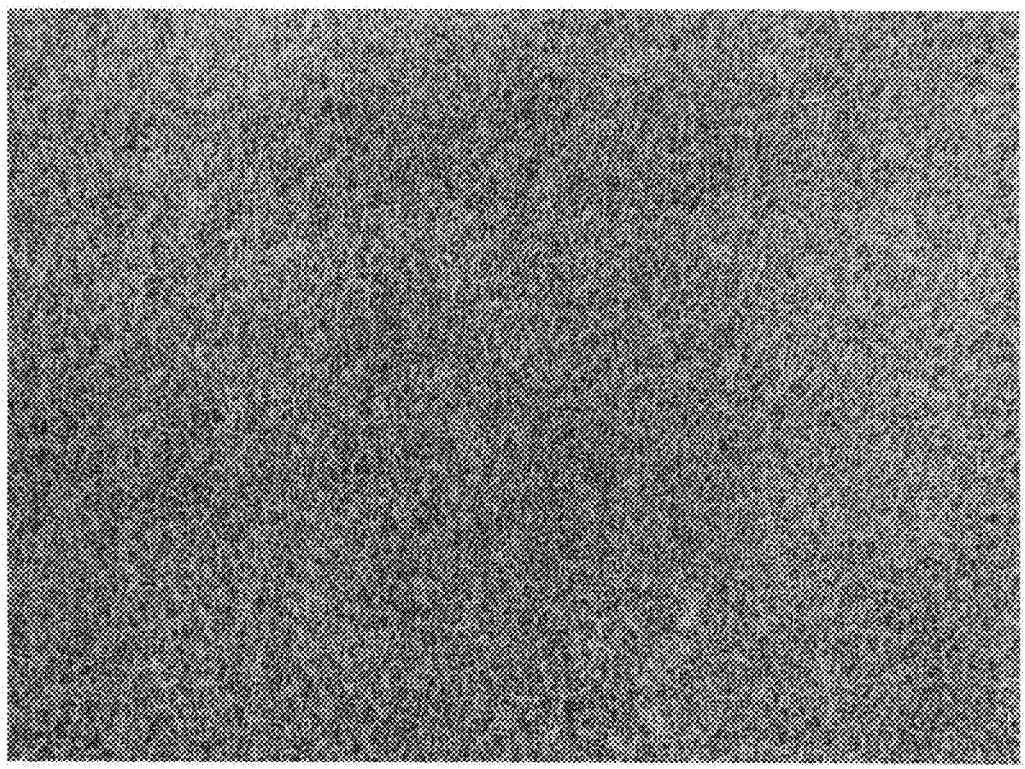
FIG. 1, taken on Oct. 24, 2008, shows a digital image of turf response of 'JS501', after a TOUCHDOWN TOTAL® glyphosate herbicide spray treatment, administered at 8 ounces per acre, was applied on Sep. 12, 2008.
Figure 2:
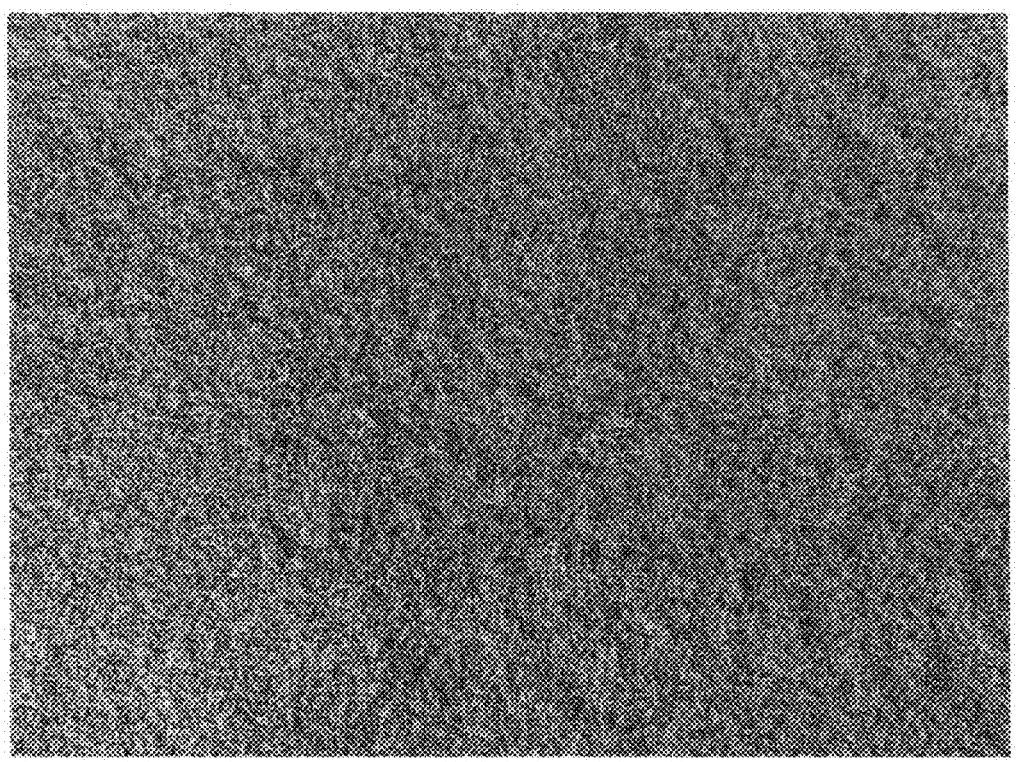
FIG. 2, taken on Sep. 12, 2008, shows a digital image of turf response of 'JS501', after a TOUCHDOWN TOTAL® glyphosate herbicide spray treatment, administered at 8 ounces per acre, was applied on Aug. 7, 2008.

The following definitions and methods are provided to better define the present invention and to guide those of ordinary skill in the art in the practice of the present invention. Unless otherwise noted, terms and phrases are to be understood according to conventional usage by those of ordinary skill in the relevant art. Standard techniques are used for asexual and sexual reproduction methods, as well as, molecular reproduction procedures. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 C.F.R. §1.822 is used.

A. Definitions

1. Agricultural Terms

Angiosperm is defined as vascular plants having seeds enclosed in an ovary. Angiosperms are seed plants that produce flowers that bear fruits. Angiosperms are divided into dicotyledonous and monocotyledonous plants.

Dicotyledonous plant (Dicot) is defined as a flowering plant whose embryos have two seed halves or cotyledons, branching leaf veins, and flower parts in multiples of four or five. Examples of dicots include but are not limited to, *Eucalyptus, Populus, Liquidamber, Acacia,* teak, mahogany, cotton, tobacco, *Arabidopsis*, tomato, potato sugar beet, broccoli, cassava, sweet potato, pepper, poinsettia, bean, alfalfa, soybean, carrot, strawberry, lettuce, oak, maple, walnut, rose, mint, squash, daisy, geranium, avocado, and cactus.

Monocotyledonous Plant (Monocot) is defined as a flowering plant having embryos with one cotyledon or seed leaf, parallel leaf veins, and flower parts in multiples of three. Examples of monocots include, but are not limited to turfgrass, maize, rice, oat, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (Kentucky bluegrass), *Lolium* spp. (ryegrass species including annual ryegrass and perennial ryegrass), *Festuca arundinacea* (tall fescue) *Festuca rubra commutata* (Chewings fescue), *Cynodon dactylon* (bermudagrass); *Pennisetum clandestinum* (kikuyu grass), *Stenotaphrum secundatum* (St. Augustine grass), *Zoysia japonica* (zoysia grass), and *Dichondra micrantha*.

A cultivar or variety is a group of similar plants which belong to the same species and which by structural features and performance may be distinguished from other varieties within the same species. Two essential characteristics of a variety are identity and reproducibility. Identity is necessary so that the variety may be recognized and distinguished from other varieties within the crop species. The distinguishing features may be morphological characteristics, color markings, physiological functions, disease reaction, or performance. Most agricultural varieties are pure for those characteristics which identify the variety. Reproducibility is needed so that the characteristics by which the variety is identified will be reproduced in the progeny. A variety is derived from a strain; populations which are increased from a single genotype or a mixture of genotypes are referred to as strains, experimental strains, or lines. Once a strain is identified as superior, it may be named, increased, and made available commercially as a "cultivated variety" or "cultivar." The words "variety" and "cultivar" are used interchangeably, although cultivar is commonly used in scientific literature while variety is the term used by U.S. farmers and the seed trade.

In the present invention, cultivar and/or variety is defined as equivalent to clone, as a glyphosate tolerant diploid perennial ryegrass cultivar may individually be reproduced asexually and all of the clones are essentially identical genetically.

Progeny is defined as the subsequent generation following a crossing of parental plants. Progeny in the present invention may also be considered to be the offspring or descendants of a group of plants.

In another embodiment of the present invention, progeny may be defined as the progeny of a transgenic plant—one that is born of, begotten by, or derived from a plant or the transgenic plant. Thus, a progeny plant, i.e., an $F_1$ generation plant is an offspring or a descendant of the transgenic plant produced by the methods described herein. A progeny of a transgenic plant may contain in at least one, some, or all of its cell genomes, the desired polynucleotide that was integrated into a cell of the parent transgenic plant by the methods described herein. Thus, the isolated polynucleotide is transmitted or inherited by the progeny plant. The isolated polynucleotide that is inherited in the progeny plant may reside within a T-DNA construct, which also is inherited by the progeny plant from its parent. In the present invention, the isolated polynucleotide that is inherited in a perennial ryegrass 'JS501' progeny is an isolated perennial ryegrass 5-enolpyruvylshikimate 3-phosphate synthase (EPSPS) polynucleotide comprising the nucleotide sequence of SEQ ID NO:10.

Plant Parts are defined in the present invention, as plant parts of a perennial ryegrass including, but not limited to, leaves, collar, embryos, cotyledons, hypocotyls, seeds, meristematic cells, flowers, anthers, pollen, tillers, roots, root tips, stems, culms, stolons, rhizomes, crown, sprigs and plugs.

Plant Tissue is defined as any plant tissue of a part of a plant including, but are not limited to, leaves, collar, somatic embryos, cotyledons, hypocotyls, seeds, meristematic cells, flowers, anthers, pollen, tillers, roots, root tips, stems, calli, culms, stolons, rhizomes, crown, microtubers, shoots, sprigs and plugs, that may be treated according to the methods of the present invention to produce a glyphosate tolerant plant. Thus, the present invention envisions the transformation of plants, wherein the transformation confers glyphosate tolerance of the transformed plant compared to a wild-type or non-transformed plant.

In the present invention plant tissue is defined to also encompass plant cells. Plant cells include, but are not limited to, suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, hybrid, propagule whether generated sexually or asexually, and descendents of any of these, such as cuttings or seed.

In the present invention, tissue culture is defined to refer to composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, including, but are not limited to, leaves, collar, somatic embryos, cotyledons, hypocotyls, seeds, meristematic cells, flowers, anthers, pollen, tillers, roots, root tips, stems, calli, culms, stolons, rhizomes, crown, microtubers, shoots, sprigs and plugs. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

In the present invention, the term plant includes plant parts, plant tissue, plant cells, plant protoplasts, plant cell tissue cultures from which plants can be regenerated, plant calli, plant clumps, and plant cells that are intact in plants or parts of plants, including, but are not limited to, leaves, collar, somatic embryos, cotyledons, hypocotyls, seeds, meristematic cells, flowers, anthers, pollen, tillers, roots, root tips, stems, calli, culms, stolons, rhizomes, crown, microtubers, shoots, sprigs and plugs. Plants contemplated for use in the practice of the present invention include both monocotyledons and dicotyledons. Preferably, the plant for use in the present invention is perennial ryegrass.

Harvested Products are defined in the present invention, as harvested products obtained from a perennial ryegrass, including, but not limited to, seed blends and mixtures; turfgrass sprigs, plugs and sod; and fodder blends and mixtures.

Turf is defined as a species or variety/cultivar, or mixture or blend of mowed vegetation, usually a turfgrass, growing with an upper stratum of intermingled roots and stems.

Turf Color is defined as a composite visual and digital analysis score of a turfgrass community. Typically turf color, when perceived by the human eye, is a subjective measure of the amount of lightness or darkness of green color, usually measured using a 1-9 visual scale, with 9 being the darkest.

Turf Density is defined as the number of grass tillers or shoots per unit area of a turfgrass sward, and is measured at a specific time after seeding. In the present invention, turfgrass density is measured using a 1-9 visual scale, with 9 being most dense.

Turf Damage is defined in the present invention as the degree of damage to a turf (characterized by wilting, reduced growth, and yellowing of turf), after application of a glyphosate-based herbicide. Turf damage is generally taken as subjective data measured using a 1-9 visual scale, with 9 being no damage and 1 being complete damage, and is measured at different time intervals after application of a glyphosate-based herbicide.

Turf Environment is defined as the complex of climate, edaphic, biotic, and cultural (management) factors that act upon a turfgrass community and ultimately determine the turfgrass' form and survival.

Turf Quality is defined as the degree to which a turf conforms to a standard of uniformity, density, texture, growth habit, texture, and color, and is generally taken as subjective data measured using a 1-9 visual scale, with 1 being bare soil and 9 being perfect turf.

Plant Height is defined as the height of a fully headed (mature) unmowed plant measured from the ground to the tip of the tallest inflorescence spike (seed head), and is measured in cm.

Plant Maturity is defined as by the timing of the appearance of the seed head of a grass plant, and is described using the terms, early, medium, and late, including any combination (e.g., early-medium).

Plant Growth Habit is defined as the degree of erectness of a single plant, when using a 1-9 visual scale, 1=prostrate (flat), 2=semi-prostrate, 3=horizontal, 7=semi-erect, 9=erect.

Seedling Vertical Growth Rate is defined as the measurement of the height of the longest expanded leaf (tallest leaf), and is measured at plant maturity.

Seedling Vigor is defined as the robustness of seedling growth rate, and is described using a 1-9 visual scale to represent terms low, moderate and high, including any combination (e.g., low-moderate), with 9-high.

Seed Weight is defined as the weight of 100 pure, whole seeds of a variety.

Culm is defined as the central axis of the mature, aboveground, upright reproductive stem, comprised of nodes and internodes, with each node bearing a leaves. Culm Length is the measurement of the length of the mature, central axis reproductive stem, measured from the crown growing point (below ground) to the peduncle tip, and is measured in cm.

Node is defined as the joint on a culm (stem) of a grass plant. At a node of a grass plant, a bud, leaf or aerial root may grow. Internode is defined as the distance between two nodes.

Collar Region is defined as a region consisting of the parts of a grass leaf, namely the leaf blade, the leaf sheath, auricles, and the ligule, together with a thin band of meristematic tissue at the junction of the leaf blade and the sheath, referred to as the collar, and which is responsible for leaf blade growth.

Leaf Sheath is defined as the lower part of a leaf, and is the flat, blade-like portion that actions like a petiole, and surrounds the culm (stem) the distance to the internode below. Leaf Sheath Length is the measurement of the length of the Leaf Sheath of the first leaf subtending the Flag Leaf, and is measured in cm.

Leaf Blade (also known as the lamina) is defined as a part of a grass leaf, and extends at a right angle above the leaf sheath. Leaf Blade Length is the measurement of the length of the first Leaf Blade subtending the Flag Leaf and is measured in cm. Leaf Blade Width is the measurement of the width of the first Leaf Blade subtending the Flag Leaf, taken 1 cm from the collar, and is measured in mm. Leaf Blade Height is the measurement of the height of the Leaf Blade from the ground to the collar, and is measured in cm.

Flag Leaf is defined as the uppermost leaf of the culm (the first leaf which encloses the seed head (inflorescence) during the boot stage and is positioned below the seed head (inflorescence) at reproductive maturity), and measured in cm. Flag Leaf Length is the measurement of the total length of a flag leaf (including both the leaf blade and leaf sheath, taken from the uppermost node to the end of the upper most leaf blade, and is measured in cm. Flag Leaf Width is the measurement of the width of the flag leaf blade, taken 1 cm from the collar, and measured in mm. Flag Leaf Height is the measurement of the height of the flag leaf, taken from the ground to the collar of the flag leaf, and measured in cm. Flag Leaf Sheath Length is the measurement of the sheath length of the flag leaf, taken from the node to the collar, and measured in cm.

Ligule is defined as part of a grass leaf, and is a small, tongue-like flap of membranous tissue that is a modified extension of the sheath; often a vertical extension, but in some instances, can be bristles. Ligule Length is the measurement of the length of the membranous tissue protrusion on the adaxial side of the leaf collar at the junction of the leaf blade and leaf sheath, and is measured in mm.

Auricles are defined as a part of a grass leaf, and are two (2) small, claw-like, membranous appendages that 1) extend perpendicular from the base of the leaf blade, 2) run parallel to the leaf sheath, and 3) partially surround the culm (stem).

Leaf Texture is defined as the relative fineness or coarseness of turfgrass leaves.

Inflorescence (seed head) is defined as the flower head of a grass plant. In a grass plant, the flower head terminates the stem and consists of florets (flowers) arranged on a common axis.

Spike is defined as the basic floral unit of a grass inflorescence, comprised of glumes, lemmas, paleas and florets. Spike Length is measured from the upper most node to the apex of the inflorescence, and measured in cm.

Rachis (peduncle) is defined as the upper most culm segment supporting the inflorescence (seed head).

Glume is defined as the pair of chaffy bracts at the base of a spikelet of a grass plant, which encloses the immature florets.

Lemma is defined as the longer (outer), chaffy floral bract, which protects an individual floret. An awn, a fibrous bristle (beard) may extend from the lemma.

Palea is defined as the shorter, (inner) floral bract, which protects an individual floret.

Floret is defined as the reproductive unit of a grass spikelet that include a lemma, palea and reproductive organs. The lemma together with the palea provide a protective covering for the developing floret and the seed after ripening.

Seed is defined as a ripened plant ovule containing an embryo, and a propagative part of a plant. In plant transformation, seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Overseeding is defined as the process of spreading grass seed over an existing turfgrass. In the present invention, overseeding relates only to the use of cool-season turfgrass sown into an existing warm-season turn grass, for the purpose of having a green cover during the winter months when the warm-season grass is dormant.

Pollination is defined as the transfer of pollen from the anther to the stigma of the same or a different flower to ensure fertilization of the ovules to produce seeds. In the present invention, the method of pollination used to produce glyphosate tolerant perennial ryegrass may include self-pollination, open pollination, wind pollination, controlled pollination, or mass controlled pollination.

Glyphosate is defined as N-phosphonomethylglycine and its salts. Glyphosate is the active ingredient of TOUCHDOWN TOTAL® herbicide (Syngenta Crop Protection, Inc. (Greensboro, N.C.). Treatments with glyphosate herbicide or glyphosate-based herbicide is defined as treatments with the TOUCHDOWN TOTAL® herbicide or any other formulation containing glyphosate. For the purposes of the present invention, the term glyphosate includes any herbicidally active form of N-phosphonomethylglycine (including any salt thereof) and other forms that result in the production of the glyphosate anion in plants. Plant transformation and regeneration in tissue culture use glyphosate or salts of glyphosate. Whole plant assays use formulated TOUCHDOWN TOTAL®, unless otherwise stated. Additional formulations with herbicide activity that contain N-phosphonomethylglycine or any of its salts are herein included as a glyphosate herbicide.

Effective Rate of Glyphosate is defined as the effective rate of glyphosate herbicide which can be applied to a plant for weed control without significantly affecting the plant. In the present invention, the effective rate of glyphosate, which can be applied to the glyphosate tolerant 'Intercept TD' plant, or the progeny or hybrid plants thereof, includes but is not limited to, up to 16 ounces per acre. In the present invention, the effective rate of glyphosate which can be applied to a glyphosate tolerant plant, or the progeny or hybrid plants thereof, includes but is not limited to, at least 8 ounces per acre, at least 16 ounces per acre, or greater amounts, such as, at least 20 ounces per acre.

Treatments with glyphosate in the present invention refer to treatments with the TOUCHDOWN TOTAL® herbicide formulation.

Glyphosate Tolerance is defined as the resistance impaired by mutant 5-enolpyruvl-3-phosphikimate synthase (EPSPS) and aroA genes, respectively) and other phosphono compounds such as glufosinate (phosphinothricin acetyl transferase, PAT and *Streptomyces* hygroscopicus phosphinothricin-acetyl transferase, bar, genes), and pyridinoxy or phenoxy proprionic acids and cycloshexones (ACCase inhibitor-encoding genes). See, for example, U.S. Pat. No. 4,940,835, which discloses the nucleotide sequence of a form of EPSPS which can confer glyphosate tolerance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricin-acetyl-transferase gene is provided in European application No. 0 242 246, and DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop are the Acc1-S1, Acc1-S2, and Acc2-S3 genes described by Marshall et al., Theor. Appl. Genet. 83:435 (1992). In the present invention, glyphosate tolerance is described using the terms, none, low, moderate, and high, including any combination (e.g., low-moderate).

Wild-type plant in the present invention is defined as a plant that has not been altered by a method of the invention and/or does not comprise a transgene of the invention. When performing a method of the invention, the manipulated plant is compared to a non-manipulated ("wild-type") member of the same species to determine the tolerance to glyphosate.

A trademark, otherwise known as a brand, may be a word, name, symbol, device, design or phrase adopted and used to identify its goods and services and to distinguish them from the goods and services of others.

TD™ brand plants are perennial rypegrass cultivars of the present invention that exhibit tolerance to glyphosate-based herbicides.

2. Molecular Terms

Allele is defined as any of one or more alternative forms of a gene, all of which alleles relate to one trait or characteristic. In a diploid cell or organism, the two alleles of a given gene occupy corresponding loci on a pair of homologous chromosomes.

*Agrobacterium* or Bacterial Transformation is well known in the field, Agrobacteria that are used for transforming plant cells are disarmed and virulent derivatives of, usually, *Agrobacterium tumefaciens, Agrobacterium rhizogenes*, that contain a vector. The vector typically contains a desired polynucleotide that is located between the borders of a T-DNA. However, any bacteria capable of transforming a plant cell may be used, such as, *Rhizobium trifolii, Rhizobium leguminosarum, Phyllobacterium myrsinacearum, SinoRhizobium meliloti*, and *MesoRhizobium loti*.

Amplification of DNA/amplified DNA is defined as the product of nucleotide amplification of a target nucleotide sequence. Nucleotide amplification can be accomplished by any of the various nucleotide amplification methods known in the art, including the polymerase chain reaction (PCR). A variety of amplification methods are known in the art and are described, inter alia, in U.S. Pat. Nos. 4,683,195 and 4,683,202, and in Innis et al. (eds.), PCR Protocols: A Guide to Methods and Applications, Academic Press, San Diego, 1990.

Construct is defined as a construct comprising a vector and an insert operatively linked to the vector, such that the vector and insert can be replicated and transformed as required.

Desired Polynucleotide of the present invention is defined as a genetic element, such as a promoter, enhancer, or terminator, or gene or polynucleotide that is to be transcribed and/or translated in a transformed plant cell that comprises the desired polynucleotide in its genome. If the desired polynucleotide comprises a sequence encoding a protein product, the coding region may be operably linked to regulatory elements, such as to a promoter and a terminator, that bring about expression of an associated messenger RNA transcript and/or a protein product encoded by the desired polynucleotide. Thus, a desired polynucleotide may comprise a gene that is operably linked in the 5'- to 3'-orientation, a promoter, a gene that encodes a protein, and a terminator. Alternatively, the desired polynucleotide may comprise a gene or fragment thereof, in a "sense" or "antisense" orientation, the transcription of which produces nucleotides that may affect expression of an endogenous gene in the plant cell. A desired polynucleotide may also yield upon transcription a double-stranded RNA product upon that initiates RNA interference of a gene to which the desired polynucleotide is associated. A desired polynucleotide of the present invention may be positioned within a T-DNA, such that the left and right T-DNA border sequences flank or are on either side of the desired polynucleotide. The present invention envisions the stable integration of one or more desired polynucleotides into the genome of at least one plant cell. A desired polynucleotide may be mutated or a variant of its wild-type sequence. It is understood that all or part of the desired polynucleotide can be integrated into the genome of a plant. It also is understood that the term desired polynucleotide encompasses one or more of such polynucleotides.

Endogenous is defined as a nucleotide, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species.

Expression is defined as the generation of a protein product derived from a DNA sequence encoding the protein, comprising a combination of transcription and translation. An expression cassette refers to a nucleotide sequence comprising a promoter in operable relationship with an open reading frame, or a complement thereof.

Foreign is defined with respect to a nucleotide, and means that that nucleotide is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleotides that are not naturally occurring in the plant that is to be transformed. Thus, a foreign nucleotide is one that encodes, for instance, a polypeptide that is not naturally produced by the transformed plant.

Gene is defined as a segment of a DNA molecule that contains all the information required for synthesis of a product, polypeptide chain or RNA molecule that includes both coding and non-coding sequences.

Genetic Element is defined as any discreet nucleotide sequence such as, but not limited to, a promoter, gene, terminator, intron, enhancer, spacer, 5'-untranslated region, 3'-untranslated region, or recombinase recognition site.

Genetic Modification is defined as any stable introduction of DNA into the genome of certain organisms by applying methods in molecular and cell biology.

Introduction is defined as the insertion of a nucleotide sequence into a plant cell, by methods such as infection, transfection, transformation or transduction.

Host cell is defined as any cell that can be transformed with a polynucleotide of the present invention. Host cells can be either untransformed cells or cells that are already transformed with at least one nucleic acid molecule (e.g., nucleic acid molecules encoding one or more proteins of the present invention). Host cells of the present invention either can be endogenously (i.e., naturally) capable of producing proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite, arthropod, animal and plant cells. Preferred host cells are plant cells, in particular perennial ryegrass cells.

Kill Curve is defined as the frequency of shoot regeneration/explant for increasing concentrations of a chemical, whereby relatively high concentrations prevent regeneration, and result in eventual death of the explants. The lowest concentration of the chemical that prevents shoot regeneration is the minimal concentration that can be used to select for transformed plant cells, whereby the selectable marker gene is a gene that provides tolerance against the chemical, thus, allowing transgenic shoot formation. The optimized concentration of the chemical to be used for plant transformation experiments is a concentration that is higher than the minimal concentration but still allows the selectable marker gene to confer tolerance to the transformed cell to produce a transformed shoot and, consequently, a transformed plant.

Native as used herein, is defined as a nucleotide, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species.

Native Glyphosate Tolerant Gene is defined as an 5-enolpyruvylshikimate 3-phosphate synthase (EPSPS) gene isolated from a plant species that is isolated either from the genome of a plant or plant species that is to be transformed or is isolated from a plant or species that is sexually compatible or interfertile with the plant species that is to be transformed, is "native" to, i.e., indigenous to, the plant species. In the present invention, native glyphosate tolerant gene is defined as isolated perennial ryegrass 5-enolpyruvylshikimate 3-phosphate synthase (EPSPS) polynucleotide comprising the nucleotide sequence of SEQ ID NO:10.

Native DNA is defined as any nucleotide, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleotide also are considered "native" in accordance with the present invention. For instance, a native DNA may comprise a point mutation since such point mutations occur naturally. It is also possible to link two different native DNAs by employing restriction sites because such sites are ubiquitous in plant genomes.

Native Nucleotide Construct is defined as a polynucleotide comprising at least one native DNA.

Operably linked as used herein, is defined as combining two or more molecules in such a fashion that in combination they function properly in a plant cell. For instance, a promoter is operably linked to a structural gene when the promoter controls transcription of the structural gene.

P-DNA is defined as a plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterum* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. See Rommens et al. in WO2003/069980, US-2003-0221213, US-2004-0107455, and WO2005/004585, which are all incorporated herein by reference.

Phenotype is defined as a distinguishing feature or characteristic of a plant, which may be altered by integrating one or more isolated polynucleotides and/or screenable/selectable markers into the genome of at least one plant cell of a transformed plant. The isolated polynucleotides and/or markers may confer a change in the phenotype of a transformed plant, by modifying any one of a number of genetic, molecular, biochemical, physiological, morphological, or agronomic characteristics or properties of the transformed plant cell or plant as a whole. In the present invention, expression of one or more, stably integrated isolated polynucleotides comprising the nucleotide sequence of SEQ ID NO:10 in a plant genome, yields a phenotype of glyphosate tolerance.

Polynucleotide is defined as a nucleotide sequence, comprising a gene coding sequence or a fragment thereof, (comprising at least 15 consecutive nucleotides, preferably at least 30 consecutive nucleotides, and more preferably at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

Isolated Polynucleotide is defined as polynucleotide sequence that is not in its native state, e.g., the polynucleotide is comprised of a nucleotide sequence not found in nature or the polynucleotide is separated from nucleotide sequences with which it typically is in proximity or is next to nucleotide sequences with which it typically is not in proximity. In the present invention, an isolated polynucleotide refers to an isolated perennial ryegrass 5-enolpyruvylshikimate 3-phosphate synthase (EPSPS) polynucleotide comprising the nucleotide sequence of SEQ ID NO:10.

Polymorphism is defined in the present invention to denote a variation in the nucleotide sequence of gene(s) of the invention, between different species, cultivars, strains or individuals of a plant. A polymorphic position is a preselected nucleotide position within the sequence of the gene. In some cases, genetic polymorphisms are reflected by an amino acid sequence variation, and thus, a polymorphic position can result in location of a polymorphism in the amino acid sequence at a predetermined position in the sequence of a polypeptide. Typical polymorphisms are deletions, insertions or substitutions. These can involve a single nucleotide (single nucleotide polymorphism or SNP) or two or more nucleotides. A deletion, as used herein, refers to a change in either amino acid or nucleotide sequence in which one or more amino acid or nucleotide residues, respectively, are absent. An insertion or addition, as used herein, refers to a change in an amino acid or nucleotide sequence resulting in the addition of one or more amino acid or nucleotide residues, respectively. A substitution, as used herein, refers to the replacement of one or more amino acids or nucleotides by different amino acids or nucleotides, respectively.

In the present invention, any molecular biological technique known in the art which is capable of detecting a polymorphism/mutation/genetic variation or differential gene expression can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage, or a combination thereof (see, for example, Lemieux, 2000). The invention also includes the use of molecular marker techniques to detect polymorphisms closely linked to genes of the invention. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis.

Polymerase Chain Reaction (PCR) is defined as a reaction in which replicate copies are made of a target polynucleotide using a pair of primers or set of primers consisting of upstream and a downstream primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells expressing, or that should be expressing, a gene of the invention. However, it will generally be easier if PCR is performed on genomic DNA isolated from a plant.

Promoter is defined as a nucleotide, preferably DNA that binds RNA polymerase and/or other transcription regulatory elements. As with any promoter, the promoters of the current invention will facilitate or control the transcription of DNA or RNA to generate an mRNA molecule from a nucleotide molecule that is operably linked to the promoter. Several types of promoters are well known in the transformation arts, as are other regulatory elements that can be used alone or in combination with promoters.

Plant Promoter is defined as a promoter capable of initiating transcription in plant cells whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as leaves, roots, seeds, fibers, xylem vessels, tracheids, or sclerenchyma. Such promoters are referred to as tissue preferred promoters. Promoters which initiate transcription only in certain tissues are referred to as tissue-specific promoters. A cell type-specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

In the present invention, an inducible promoter is operably linked to a gene for expression in perennial ryegrass. Optionally, the inducible promoter is operably linked to a nucleotide sequence encoding a signal sequence which is operably linked to a gene for expression in perennial ryegrass. With an inducible promoter the rate of transcription increases in response to an inducing agent. Any inducible promoter can be used in the present invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Hershey et al., *Mol. Gen Genetics* 227: 229-237 (1991) and Gatz et al., *Mol. Gen. Genetics* 243:32-38 (1994)) or Tet repressor from Tn10 (Gatz et al., *Mol. Gen. Genetics* 227:229-237 (1991). A preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. See Schena et al., *Proc. Natl. Acad. Sci. USA* 88:0421 (1991).

In the present invention, an constitutive promoter is operably linked to a gene for expression in perennial ryegrass or the constitutive promoter is operably linked to a nucleotide sequence encoding a signal sequence which is operably linked to a gene for expression in perennial ryegrass. Many different constitutive promoters can be utilized in the present invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a useful constitutive promoter. See PCT application WO96/30530.

In the present invention, tissue-specific or tissue preferred promoter is operably linked to a gene for expression in perennial ryegrass. Optionally, the tissue-specific promoter is operably linked to a nucleotide sequence encoding a signal sequence which is operably linked to a gene for expression in perennial ryegrass. Plants transformed with a gene of interest operably linked to a tissue-specific promoter produce the protein product of the transgene exclusively, or preferentially, in a specific tissue. Any tissue-specific or tissue-preferred promoter can be utilized in the present invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. USA* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13

(Guerrero et al., *Mol. Gen. Genetics* 244:161-168 (1993)) or a microspore-preferred promoter such as that from apg (Twell et al., *Sex. Plant Reprod.* 6:217-224 (1993)).

Selectable/Screenable Marker is defined as a gene that, if expressed in plants or plant tissues, makes it possible to distinguish them from other plants or plant tissues that do not express that gene. Screening procedures may require assays for expression of proteins encoded by the screenable marker gene. Examples of selectable markers include the neomycin phosphotransferase (NPTII) gene encoding kanamycin and geneticin resistance, the hygromycin phosphotransferase (HPT or APHIV) gene encoding resistance to hygromycin, or other similar genes known in the art.

Sequence Identity is defined in the context of two nucleotide or polypeptide sequences, and includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have sequence similarity. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11-17 (1988) e.g., as implemented in the program PC/GENE (Intelligenetics, Mountain View, Calif., USA).

Sequence Identity has an art-recognized meaning and can be calculated using published techniques. See COMPUTATIONAL MOLECULAR BIOLOGY, Lesk, ed. (Oxford University Press, 1988), BIOCOMPUTING: INFORMATICS AND GENOME PROJECTS, Smith, ed. (Academic Press, 1993), COMPUTER ANALYSIS OF SEQUENCE DATA, PART I, Griffin & Griffin, eds., (Humana Press, 1994), SEQUENCE ANALYSIS IN MOLECULAR BIOLOGY, Von Heinje ed., Academic Press (1987), SEQUENCE ANALYSIS PRIMER, Gribskov & Devereux, eds. (Macmillan Stockton Press, 1991), and Carillo & Lipton, *SIAM J. Applied Math.* 48: 1073 (1988). Methods commonly employed to determine identity or similarity between two sequences include but are not limited to those disclosed in GUIDE TO HUGE COMPUTERS, Bishop, ed., (Academic Press, 1994) and Carillo & Lipton, supra. Methods to determine identity and similarity are codified in computer programs. Preferred computer program methods to determine identity and similarity between two sequences include but are not limited to the GCG program package (Devereux et al., *Nucleotides Research* 12: 387 (1984)), BLASTP, BLASTN, FASTA (Atschul et al., *J. Mol. Biol.* 215: 403 (1990)), and FASTDB (Brutlag et al., *Comp. App. Biosci.* 6: 237 (1990)).

Percentage of Sequence Identity is defined as the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide base or amino acid residue occurs in both sequences to yield the number of matched positions, dividing the number of matched positions by the total number of positions in the window of comparison and multiplying the result by 100 to yield the percentage of sequence identity.

Signal Sequences for Targeting Proteins to Subcellular Compartments refers to the transport of protein produced by transgenes to a subcellular compartment such as the chloroplast, vacuole, peroxisome, glyoxysome, cell wall or mitochondrion or for secretion into the apoplast, and is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Frontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., "A short amino acid sequence able to specify nuclear location," *Cell* 39:499-509 (1984), Steifel, et al., "Expression of a maize cell wall hydroxyproline-rich glycoprotein gene in early leaf and root vascular differentiation," *Plant Cell* 2:785-793 (1990).

Foreign Protein Genes and Agronomic Genes is defined in the present invention as foreign protein that can be produced in commercial quantities for transgenic plants. Techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981). In the present invention, a transgenic plant provided for commercial production of foreign protein may be a perennial ryegrass plant and the biomass of interest may be perennial ryegrass seed. Likewise, by means of the present invention, agronomic genes can be expressed in transformed plants. More particularly, plants can be genetically engineered to express various phenotypes of agronomic interest.

For the number of transgenic or transformed plants that show higher levels of expression of the gene, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Transcriptional Terminator is defined as an expression DNA construct that has a transcriptional termination region at the opposite end from the transcription initiation regulatory region. The transcriptional termination region may be selected, for stability of the mRNA to enhance expression and/or for the addition of polyadenylation tails added to the gene transcription product. Translation of a nascent polypeptide undergoes termination when any of the three chain-termination codons enters the A site on the ribosome. Translation termination codons are UAA, UAG, and UGA. Transcription terminators may be derived from either a gene or, more preferably, from a sequence that does not represent a gene but intergenic DNA.

Transfer DNA (T-DNA) is defined as an *Agrobacterium* T-DNA is a genetic element that is well-known as an element capable of integrating a nucleotide sequence contained within its borders into another genome. In this respect, a T-DNA is flanked, typically, by two border sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleotides, like promoter and terminator regulatory elements that facilitate its expression, i.e., transcription and/or translation of the DNA sequence encoded by the desired polynucleotide or selectable marker.

Transformation of Plant Cells is defined as a process by which a nucleotide sequence is stably inserted into the genome of a plant cell (e.g. a vector, construct or recombinant DNA molecule). Transformation may occur under natural or artificial conditions using various methods well known in the art. Transformation may rely on any known method for the insertion of nucleotide sequences into a prokaryotic or eukaryotic host cell, including *Agrobacterium*-mediated transformation protocols such as 'refined transformation' or 'precise breeding', viral infection, whiskers, electroporation, microinjection, polyethylene glycol-treatment, heat shock, lipofection and particle bombardment. After completion of the plant cell transformation process, the genetically modified plant cells are transferred to an appropriate plant culture medium for maintenance, further growth, and/or further development. Such cell culture methods are well known to the skilled artisan.

Transgenic Event is produced by transformation of plant cells with heterologous DNA, i.e., a polynucleotide construct that includes a transgene of interest, regeneration of a population of plants resulting from the insertion of the transgene into the genome of the plant, and selection of a particular plant characterized by insertion into a particular genome location. The term event refers to the original transformant and progeny of the transformant that include the heterologous DNA. The term event also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term event also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. It is also to be understood that two different transgenic plants can also be mated to produce offspring that contain two independently segregating added, exogenous genes.

In the present invention, one embodiment of an event comprises perennial ryegrass 'Intercept TD1' seed comprising the EPSPS polypeptide of SEQ ID NO:13 and grass plants grown from the seed, as well as, the progeny and hybrids, plant parts, and harvested products thereof, all of which comprise the EPSPS polypeptide of SEQ ID NO:13.

Another embodiment of an event comprises a perennial ryegrass plant comprising the EPSPS polypeptide of SEQ ID NO:13 that confers tolerance to an effective amount of glyphosate herbicide, and said perennial ryegrass plant can be bred by first sexually crossing a first parental glyphosate tolerant perennial ryegrass 'JS501' plant comprising the EPSPS polypeptide of SEQ ID NO:13, and a second parental non-tolerant glyphosate grass plant that lacks the EPSPS polypeptide of SEQ ID NO:13, thereby producing a plurality of first progeny grass plants; and then selecting a first progeny grass plant that is glyphosate tolerant or progeny that are heterozygous for glyphosate tolerance; and selfing the first progeny grass plants, thereby producing a plurality of second progeny grass plants; and then selecting from the second progeny plants, a glyphosate tolerant plant or progeny that are heterozygous for glyphosate tolerance. These steps can further include the back-crossing of the first progeny glyphosate tolerant grass plant or the second progeny glyphosate tolerant grass plant to a second parental grass plant or a third parental grass plant, thereby producing a glyphosate tolerant grass plant or progeny that are heterozygous for glyphosate tolerance.

Transgenic Plant is defined as a plant or progeny thereof derived from a transformed plant cell or protoplast, wherein the plant DNA contains an introduced exogenous DNA molecule not originally present in a native, non-transgenic plant of the same strain. According to the present invention, a transgenic plant is a plant that comprises only one genetically modified cell and cell genome, or is a plant that comprises some genetically modified cells, or is a plant in which all of the cells are genetically modified. A transgenic plant of the present invention may be one that comprises expression of the desired polynucleotide, i.e., the exogenous nucleotide, in only certain parts of the plant. Thus, a transgenic plant may contain only genetically modified cells in certain parts of its structure. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant.

Variant as used herein, is defined as a nucleotide or amino acid sequence that deviates from the standard, or given, nucleotide or amino acid sequence of a particular gene or protein. The terms, isoform, isotype, and analog also refer to variant forms of a nucleotide or an amino acid sequence. An amino acid sequence that is altered by the addition, removal or substitution of one or more amino acids, or a change in nucleotide sequence, may be considered a variant sequence. The variant may have conservative changes, wherein a substituted amino acid has similar structural or chemical properties, e.g., replacement of leucine with isoleucine. A variant may have nonconservative changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. Variant may also refer to a shuffled gene such as those described in Maxygen-assigned patents.

Vector is defined in the present invention as a DNA molecule capable of replication in a host cell and/or to which another DNA segment can be operatively linked so as to bring about replication of the attached segment. A plasmid is an exemplary vector.

B. Techniques

Descriptions of breeding methods that are commonly used for different traits and plants can be found in one of several reference books (e.g., Allard, 1960; Simmonds, 1979; Sneep et al., 1979; Fehr, 1987)). Genetic engineering of plants is complementing traditional breeding in the development of improved germplasm. Methods for reproduction and cultivation of turfgrasses are well known.

1. Asexual Propagation

Asexual propagation of turfgrasses is performed by vegetative means through the use of tissue culture practices, and can also be from offshoots (adventitious buds, tillers) detached from the mother plant and grown in appropriate soil conditions.

2. Sexual Reproduction

Traditionally, the development of new turfgrass cultivars requires the development and selection of turfgrass varieties, the crossing of these varieties and selection of superior hybrid crosses. Perennial ryegrass is highly self incompatible and needs to be outcrossed. Synthetic population development is used in this species using polycrosses of 5-200 plants with similar traits. Inbred lines are not obtained. Genotypes in the polycross have previously been tested for their ability to produce superior progeny. Polycrosses are set up matching plants by phenotype and they will have heterozygous genotypes with the goal of obtaining all possible intercrosses between the plants. After this the population is maintained in isolation and open pollinated. Additional breeding methods in this species include mass selection, backcrossing, and recurrent selection.

Mass and recurrent selections is used to improve populations of either self- or cross-pollinating turfgrasses. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcrossing methods can be used with the present invention to improve or introduce a trait into a variety. Backcross breeding has been used to transfer genes for a simply inherited, highly heritable trait into a desirable homozygous cultivar or inbred line which is called the recurrent parent; this terminology refers to the fact that the recurrent parent is used for several rounds in the backcrossing protocol (Poehlman & Sleper, 1994; Fehr, 1987). The source of the single gene trait to be transferred is called the nonrecurrent or donor parent; this terminology refers to the fact that the nonrecurrent parent is used only one time in the backcross protocol and therefore does not recur.

In a typical backcross technique, the original variety of interest (recurrent parent) is crossed to a second variety (donor parent) that carries the single gene of interest to be transferred. After the initial cross, individuals possessing the phenotype of the donor parent are selected and repeatedly crossed (backcrossed) 1, 2, 3, 4, 5, 6, 7, 8 or more times to the recurrent parent. The resulting progeny is expected to comprise essentially all of the desired morphological and physiological characteristics of the recurrent parent in addition to the desirable single gene trait transferred into the variety from the donor parent.

The selection of a suitable recurrent parent is an important step for a successful backcrossing procedure. The goal of a backcross technique is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference.

3. Seed Techniques

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more panicles (spikes) from each plant in a population and thresh them together to form a bulk. Part of the bulk is used to plant the next generation and part is put in reserve. The procedure has been referred to as modified single-seed descent or the panicle-bulk technique. The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

4. Molecular Techniques

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed variety or line. The present invention further envisions the transformation of plants, wherein the transformation confers glyphosate tolerance of the transformed plant compared to a wild-type or non-transformed plant.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. In the present invention, the vector can be used alone or in combination to provide transformed plants, using transformation methods as described below to incorporate transgenes into the genetic material of the plants.

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. Known selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988).

*Agrobacterium*-mediated transformation is one method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra and Moloney et al., Plant Cell Reports 8:238 (1989). See also, U.S. Pat. No. 5,563,055.

Direct Gene Transfer collectively refers to several methods of plant transformation that have been developed as an alternative to *Agrobacterium*-mediated transformation. A generally applicable method of plant surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Tech. 6:559-563 (1988), Sanford, J. C., Physiol Plant 7:206 (1990), Klein et al., Biotechnology 10:268 (1992). See also, U.S. Pat. No. 5,015,580 and U.S. Pat. No. 5,322,783.

Another method for physical delivery of DNA to plants is sonication of target cells. Zhang et al., Bio/Technology 9:996 (1991). Alternatively, liposome or spheroplast fusion have been used to introduce expression vectors into plants. Deshayes et al., EMBO J., 4:2731 (1985), Christou et al., Proc Natl Acad. Sci. USA 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of turfgrass target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait that has been engineered into a particular grass plant line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, crossing can refer to a simple X by Y cross, or the process of backcrossing, depending on the context.

Further reproduction of a grass variety can occur by tissue culture and regeneration. Tissue culture of various tissues of turfgrasses and regeneration of plants there from is well known and widely published. For example, reference may be had to (Altpeter, et al., 2000). Generation of large numbers of independently transformed fertile perennial ryegrass (*Lolium perenne* L.) plants of forage- and turf-type cultivars. Molecular Breeding 6: 519-528, 2000. Bradley, D. E., A. H. Bruneau, and R. Qu. 2001. Effects of cultivar, explants treatment, and medium supplements on callus induction and plantlet regeneration in perennial ryegrass. Intl. Turfgrass Soc. Res. J. 9: 152-156.), the disclosures of which are hereby incorporated herein in their entirety by references. Another aspect of this invention is to provide cells which upon growth and differentiation produce perennial ryegrass plants having the physiological and morphological characteristics of the glyphosate tolerant perennial ryegrass variety 'JS501' comprising the nucleotide sequence of SEQ ID NO:10.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Description of Glyphosate Tolerant Perennial Ryegrass 'JS501'

The present invention provides 'JS501' as a new and distinct glyphosate tolerant cultivar of perennial ryegrass.

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Example 1

Origin and Breeding History of 'JS501'

The new perennial ryegrass 'JS501' is a turf-type diploid (2n=2x=14) cultivar developed by the inventors in Post Falls, Id., in a controlled population improvement program that included breeding techniques, including but not limited to, selection, paired crosses and polycrosses. Perennial ryegrass plants with superior characteristics were advanced to the next cycle of breeding and inferior material discarded. The controlled population improvement program has grown to where today, more than 50,000 spaced plants and over 2,000 turf performance plots are evaluated annually.

'JS501' was developed from a greenhouse cross made in 1992 of perennial ryegrass 'APM' (registered, Reg. No. CV-185, PI 565096) pollinated by perennial ryegrass 'Birdie II' (registered, Reg. No. 133, PI 537452) in Post Falls, Id. Progeny of this cross was planted in a 1992 spaced-plant nursery in Post Falls, Id., and designated as 92-0226. An open-pollinated selection from this population, designated as 93-0736, was harvested and planted in company turf trials in Post Falls, Id., and Poolesville, Md., in 1993. In 1995, plugs of 93-0736 were pulled from the Maryland plot based on the desirable characteristics of dark green color and turf performance, and then planted in a spaced-plant nursery in Post Falls, Id. In 1996, the perennial ryegrass 96-3047 was selected from this population and planted in company turf trials in both Post Falls, Id., and Poolesville, Md.

In 1999, during the termination of the Maryland trial, 96-3047 was the only plot in the trial that was not killed when glyphosate at the rate of 2-quarts per acre was applied. Survival in the plot was estimated at 30% and plugs were pulled, coded as 99-0089, and 200 plants of 99-0089 were planted in an isolation block in the 1999 Post Falls, Id. nursery.

In the spring of 2000, a 1-pint per acre rate of glyphosate was applied twice before anthesis. Surviving plants were allowed to pollinate and their seed was bulk harvested as 00-3938. In May 2001, a 1,060-plant isolation block of 00-3938 was planted in Post Falls, Id., and a 1-pint per acre rate of glyphosate was applied in March of 2002. Days before anthesis, 35 plants were selected from the 00-3938 block based on the desirable characteristics of enhanced color, texture, and absence of disease, and moved to an isolated polycross, codes as 02-8015. Plants in this polycross were individually harvested; near equal amounts of seed were bulked, and replicated plots were planted in turf trials in August of 2002 in Idaho, Maryland, Ohio, and Illinois, and later planted in turf trials in March 2003 in California.

In 2003, approximately 50 seed from each of the 35 plants from the 02-8015 block were planted in a 1,733-plant isolation block at Post Falls, Id. Glyphosate at the rate of 1-pint per acre was applied in March 2004. Before anthesis, 64 uniform, early maturity plants were moved to an isolated polycross, and coded as 04-8008. The 04-2008 plants were harvested and the seed bulked. In 2005, the seed was used to plant a 3,560-plant isolation block at Post Falls, Id. Glyphosate at the rate of 1-pint per acre was applied in October of 2005 and then again in March of 2006. This block was rogued for uniformity and from the remaining 536 plants, seed was harvested and breeder seed coded as 'JS501' in 2006.

Example 2

Seed Management of 'JS501'

A. Seed Deposit with International Deposit Authority

A seed deposit of the glyphosate tolerant perennial ryegrass 'JS501' is deposited with the American Culture Type Collection (ATCC), 10801 University Boulevard, Manassas, Va. 20110-2209. 2500 seeds of the glyphosate tolerant perennial ryegrass 'JS501' were deposited with the ATCC on Sep. 30, 2009, and accorded ATCC Patent Deposit Designation No.: PTA-10370. The deposited seeds produce glyphosate tolerant perennial ryegrass plants that can be crossed, either as the male or female parent, to diverse genetic backgrounds of perennial ryegrass species to reproducibly and predictably produce new perennial ryegrass selections exhibiting glyphosate tolerance, according to the methods described herein.

B. Stock Seed Maintenance and Limitations of Generations

'JS501' is a stable and uniform variety. All evaluated seed lots of 'JS501' have produced turf of comparable quality. Uniformity of individual plant characteristics of 'JS501' is approximately 95%. As with any cross-pollinated, sexually reproduced species, segregation and recombination will produce some plants which deviate from the mean in each generation. The derivation frequency has been less than 5% in 3 years of production, and any variants can be identified as plants having an maturity earlier or later than the majority of the field, lighter color, coarser leaf texture, or taller plant size compared to 'JS501' plants. Variants of 'JS501' are relatively infrequent in occurrence and are routinely rogued from seedstock fields during the first year of establishment.

Recognized seed classes of 'JS501' are Foundation, Registered and Certified and the length of stand on each is 3, 3 and 6 years, respectively. Original 'JS501' breeder seed is maintained in long-term, controlled cold storage in Post Falls, Id., and should be enough to last the anticipated life of the variety. If new breeder seed is needed, the maintained 'JS501' breeder seed will be planted, rogued by the plant breeder and harvested as breeder seed.

Example 3

Characteristics of 'JS501'

'JS501' is an attractive cool season, bunch turf-type perennial ryegrass recommended for use on athletic fields, home lawns, golf courses (fairways, roughs and tees), parks, schools, and industrial sites, and forage, which can be grown in full sun or moderate shade.

The following traits have been repeatedly observed and are determined to be characteristics of the new perennial ryegrass 'JS501', which in combination distinguish this new perennial ryegrass as a new and distinct cultivar:
1. good turf density rating of 6.8, when using 1-9 visual scale;
2. good turf quality rate of 6.0, when using a 1-9 visual scale;
3. a medium green turf color rating of 6.8, when using 1-9 visual scale;
4. good seedling establishment rate of 6.5, when using 1-9 visual scale;
5. good pink snow mold resistance rate of 7.0, when using 1-9 visual scale;
6. ability to blend well with annual bluegrass (Poa annua) when grown under mown turf conditions as a lawn grass; and
7. tolerance to glyphosate-based herbicides.

The new diploid perennial ryegrass 'JS501' has not been observed under all possible environmental conditions. The phenotype of the new perennial ryegrass 'JS501' may vary with variations in a) environment such as temperature, light intensity and day length, as well as, b) growing conditions such as irrigation, fertilization, pruning and pest control, without any change in the genotype of the plant. The aforementioned photographs, together with the following observations, measurements and values, and comparisons describe plants of 'JS501' as grown in the turfgrass farm trials located in Idaho, Ohio, Maryland and Washington, under conditions which closely approximate those generally used in commercial practice.

Unless otherwise stated, the following detailed morphological description includes observations, measurements and values of 'JS501' plants near plant maturity. Quantified measurements are expressed as an average of measurements taken from a number of plants of 'JS501'. The measurements of any individual plant, or any group of plants, of the new 'JS501' variety may vary from the stated average.

A. Morphological Trials

Morphological trials were planted in two locations (Post Falls, Id. and Connell, Wash.) in 2007 and observations, measurements and values were collected from both locations near plant maturity in 2008.

The first trial near Post Falls, Id., used a randomized block design with 16 varieties in 5 replications of 20 plants. Plants were planted on 2½ foot centers. The soil is an Avonville fine gravelly silt loam soil. The second trial was planted near Connell, Wash., on a very sloped field (>15%) and the soil was a Burke very fine sandy loam. This trial also had 16 varieties planted in 5 replications. Preventative fungicide applications were applied near head emergence to control rust (Puccinia spp.) in Post Falls, Id., but were not needed in Connell, Wash. Fertilizer was applied in both fall and spring and the trials were irrigated as necessary to prevent stress. The Post Falls environment had a more prolonged winter than usual.

Both trials had some plants that were winter damaged. Measurements, observations and values were taken only on 'JS501' plants with normal growth characteristics (the n-size varied according to winter survival). Quantified measurements are expressed as an average of measurements taken from a number 'JS501' plants. The measurements of any individual plant, or any group of plants, of the new variety may vary from the stated average. Leaf color, hue, saturation, and intensity measurements were performed using WinSeedle Pro (S) (2004), version 2004b, web site regentinstruments.com software/scanner program where a lower intensity value indicates darker color. Leaf width, and seed length and width were also measured with the WinSeedle. Data analysis for both locations was performed using StatSoft, Inc. (2006). STATISTICA (data analysis software system), version 7.1. web site statsoft.com. Data were analyzed with ANOVA and means were separated with LSD using pair-wise comparisons, based on individual degrees of freedom. Prob.=Probability that the variety mean is not significantly different from the variety listed at the top of the table. For example, a value of 0.050 or less would indicate significance at the 5% level of probability.

The following Tables 1-6 identify morphological characteristics of the new perennial ryegrass 'JS501' and other perennial ryegrass cultivars at reproductive maturity taken in 2008 from the Connell, Wash. trial.

TABLE 1

Morphological characteristics of perennial ryegrasses (Lolium perenne L.) cultivars at reproductive maturity, near Connell, WA in 2008.*

| Variety | Flagleaf height (cm) | | | Sheath Length (cm) | | | Spike Length (cm) | | | Plant Height (cm) | | |
|---|---|---|---|---|---|---|---|---|---|---|---|---|
| | Means | N | prob. | Means | N | prob. | Means | N | prob. | Means | N | prob. |
| 'JS501' | 19.3 | 30 | | 5.9 | 30 | | 9.2 | 30 | | 33.4 | 30 | |
| Revenge GLX | 23.0 | 58 | 0.0000 | 5.5 | 58 | 0.1000 | 8.6 | 58 | 0.1180 | 37.6 | 58 | 0.0000 |
| Brightstar | 23.7 | 58 | 0.0000 | 6.1 | 58 | 0.5793 | 9.2 | 58 | 0.8980 | 38.7 | 58 | 0.0000 |
| Elka | 24.5 | 58 | 0.0000 | 7.0 | 58 | 0.0000 | 11.1 | 58 | 0.0000 | 39.7 | 58 | 0.0000 |
| Yorktown III | 24.2 | 58 | 0.0000 | 5.8 | 58 | 0.6115 | 9.4 | 58 | 0.5170 | 39.9 | 58 | 0.0000 |
| Pennfine | 24.7 | 45 | 0.0000 | 6.2 | 45 | 0.3480 | 8.9 | 45 | 0.4737 | 40.2 | 45 | 0.0000 |
| Accent II | 26.0 | 58 | 0.0000 | 6.1 | 58 | 0.5934 | 9.5 | 58 | 0.3395 | 41.3 | 58 | 0.0000 |
| Top Gun II | 25.1 | 58 | 0.0000 | 5.8 | 58 | 0.5505 | 9.7 | 58 | 0.1937 | 41.6 | 58 | 0.0000 |
| La Quinta | 24.5 | 58 | 0.0000 | 6.5 | 58 | 0.0270 | 10.9 | 58 | 0.0000 | 42.0 | 58 | 0.0000 |

TABLE 1-continued

Morphological characteristics of perennial ryegrasses (*Lolium perenne* L.) cultivars at reproductive maturity, near Connell, WA in 2008.*

| Variety | Flagleaf height (cm) | | | Sheath Length (cm) | | | Spike Length (cm) | | | Plant Height (cm) | | |
|---|---|---|---|---|---|---|---|---|---|---|---|---|
| | Means | N | prob. | Means | N | prob. | Means | N | prob. | Means | N | prob. |
| Manhattan II | 24.8 | 58 | 0.0000 | 6.5 | 58 | 0.0132 | 11.1 | 58 | 0.0000 | 42.2 | 58 | 0.0000 |
| 'APM' | 25.6 | 58 | 0.0000 | 6.6 | 58 | 0.0070 | 10.2 | 58 | 0.0072 | 42.3 | 58 | 0.0000 |
| Pinnacle | 26.7 | 58 | 0.0000 | 6.8 | 58 | 0.0004 | 9.9 | 58 | 0.0533 | 42.7 | 58 | 0.0000 |
| Advent | 26.2 | 58 | 0.0000 | 6.9 | 58 | 0.0001 | 10.8 | 58 | 0.0000 | 43.7 | 58 | 0.0000 |
| Monterey II | 25.3 | 58 | 0.0000 | 7.0 | 58 | 0.0000 | 10.7 | 58 | 0.0000 | 43.7 | 58 | 0.0000 |
| Monterey 3 | 28.1 | 58 | 0.0000 | 6.0 | 58 | 0.7845 | 10.0 | 58 | 0.0261 | 44.0 | 58 | 0.0000 |
| Caddieshack II | 26.8 | 57 | 0.0000 | 6.0 | 58 | 0.6466 | 9.9 | 58 | 0.0447 | 44.2 | 58 | 0.0000 |
| 'Intercept TD' | 26.4 | 58 | 0.0000 | 6.6 | 58 | 0.0047 | 10.5 | 58 | 0.0004 | 44.3 | 58 | 0.0000 |
| Goalkeeper II | 27.5 | 58 | 0.0000 | 6.9 | 58 | 0.0002 | 10.7 | 58 | 0.0000 | 45.5 | 58 | 0.0000 |
| Linn | 26.8 | 58 | 0.0000 | 8.5 | 58 | 0.0000 | 12.3 | 57 | 0.0000 | 46.2 | 58 | 0.0000 |
| Group Mean | 25.4 | 1176 | | 6.5 | 1177 | | 10.2 | 1176 | | 42.0 | 1177 | |
| Duncan's LSD$_{0.05}$ | 1.77 | | | 0.56 | | | 0.81 | | | 2.25 | | |
| CV % | 16.5 | | | 20.9 | | | 19.2 | | | 13.3 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.

TABLE 2

Morphological characteristics of perennial ryegrasses (*Lolium perenne* L.) cultivars at reproductive maturity, near Connell, WA in 2008.*

| Variety | Flagleaf Position | | | Flagleaf Categories | | | | | |
|---|---|---|---|---|---|---|---|---|---|
| | | | | % Erect | | | % Semi erect | | |
| | Means | N | prob. | Means | N | prob. | Means | N | prob. |
| 'JS501' | 2.0 | 30 | | 0.0 | 30 | | 100.0 | 30 | |
| Pennfine | 1.9 | 28 | 0.6127 | 25.0 | 28 | 0.0682 | 67.9 | 28 | 0.0802 |
| Yorktown III | 1.9 | 34 | 0.6712 | 17.6 | 34 | 0.1898 | 76.5 | 34 | 0.1921 |
| 'Intercept TD' | 1.9 | 43 | 0.6692 | 14.0 | 43 | 0.2910 | 83.7 | 43 | 0.3579 |
| Monterey II | 1.9 | 30 | 0.8120 | 16.7 | 30 | 0.2207 | 73.3 | 30 | 0.1438 |
| 'APM' | 2.0 | 46 | 0.8725 | 13.0 | 46 | 0.3213 | 80.4 | 46 | 0.2671 |
| Caddieshack II | 2.0 | 54 | 0.8902 | 18.5 | 54 | 0.1552 | 74.1 | 54 | 0.1376 |
| Top Gun II | 2.0 | 43 | 0.9319 | 11.6 | 43 | 0.3788 | 79.1 | 43 | 0.2373 |
| Manhattan II | 2.0 | 58 | 1.0000 | 20.7 | 58 | 0.1109 | 69.0 | 58 | 0.0744 |
| Pinnacle | 2.0 | 32 | 1.0000 | 12.5 | 32 | 0.3554 | 75.0 | 32 | 0.1680 |
| Revenge GLX | 2.0 | 39 | 0.9255 | 12.8 | 39 | 0.3353 | 76.9 | 39 | 0.1958 |
| Accent II | 2.1 | 49 | 0.8205 | 10.2 | 49 | 0.4359 | 79.6 | 49 | 0.2451 |
| Linn | 2.1 | 30 | 0.6343 | 10.0 | 30 | 0.4624 | 73.3 | 30 | 0.1438 |
| Monterey 3 | 2.2 | 45 | 0.5124 | 8.9 | 45 | 0.4997 | 66.7 | 45 | 0.0592 |
| Advent | 2.2 | 55 | 0.4555 | 5.5 | 55 | 0.6749 | 76.4 | 55 | 0.1753 |
| Goalkeeper II | 2.3 | 27 | 0.2394 | 7.4 | 27 | 0.5900 | 66.7 | 27 | 0.0707 |
| Brightstar | 2.4 | 48 | 0.1901 | 10.4 | 48 | 0.4270 | 64.6 | 48 | 0.0441 |
| La Quinta | 2.4 | 47 | 0.1160 | 0.0 | 47 | 1.0000 | 72.3 | 47 | 0.1163 |
| Group Mean | 2.1 | 815 | | 12.0 | 815 | | 75.0 | 815 | |
| Duncan's LSD$_{0.05}$ | 0.41 | | | 0.20 | | | 0.27 | | |
| CV % | 32.8 | | | 2.7 | | | 0.6 | | |

| Variety | Flagleaf Categories | | | | | | | | |
|---|---|---|---|---|---|---|---|---|---|
| | % Horizontal | | | % Recurved | | | % Deflected | | |
| | Means | N | prob. | Means | N | prob. | Means | N | prob. |
| 'JS501' | 0.0 | 30 | | 0.0 | 30 | | 0.0 | 30 | |
| Pennfine | 3.6 | 28 | 0.7685 | 3.6 | 28 | 0.5226 | 0.0 | 28 | 1.0000 |
| Yorktown III | 5.9 | 34 | 0.6216 | 0.0 | 34 | 1.0000 | 0.0 | 34 | 1.0000 |
| 'Intercept TD' | 2.3 | 43 | 0.8425 | 0.0 | 43 | 1.0000 | 0.0 | 43 | 1.0000 |
| Monterey II | 10.0 | 30 | 0.4068 | 0.0 | 30 | 1.0000 | 0.0 | 30 | 1.0000 |
| 'APM' | 4.3 | 46 | 0.7090 | 2.2 | 46 | 0.6852 | 0.0 | 46 | 1.0000 |
| Caddieshack II | 3.7 | 54 | 0.7482 | 0.0 | 54 | 1.0000 | 3.7 | 54 | 0.5113 |
| Top Gun II | 9.3 | 43 | 0.4268 | 0.0 | 43 | 1.0000 | 0.0 | 43 | 1.0000 |
| Manhattan II | 3.4 | 58 | 0.7641 | 3.4 | 58 | 0.5145 | 3.4 | 58 | 0.5392 |
| Pinnacle | 12.5 | 32 | 0.2970 | 0.0 | 32 | 1.0000 | 0.0 | 32 | 1.0000 |
| Revenge GLX | 7.7 | 39 | 0.5141 | 0.0 | 39 | 1.0000 | 2.6 | 39 | 0.6563 |
| Accent II | 6.1 | 49 | 0.5977 | 2.0 | 49 | 0.7024 | 2.0 | 49 | 0.7190 |
| Linn | 13.3 | 30 | 0.2688 | 0.0 | 30 | 1.0000 | 3.3 | 30 | 0.5716 |
| Monterey 3 | 22.2 | 45 | 0.0571 | 2.2 | 45 | 0.6791 | 0.0 | 45 | 1.0000 |
| Advent | 12.7 | 55 | 0.2696 | 3.6 | 55 | 0.4931 | 1.8 | 55 | 0.7468 |

TABLE 2-continued

Morphological characteristics of perennial ryegrasses (*Lolium perenne* L.) cultivars at reproductive maturity, near Connell, WA in 2008.*

| | | | | | | | | | |
|---|---|---|---|---|---|---|---|---|---|
| Goalkeeper II | 14.8 | 27 | 0.2240 | 7.4 | 27 | 0.1867 | 3.7 | 27 | 0.5339 |
| Brightstar | 12.5 | 48 | 0.2821 | 4.2 | 48 | 0.4360 | 8.3 | 48 | 0.1425 |
| La Quinta | 19.1 | 47 | 0.1000 | 2.1 | 47 | 0.6912 | 6.4 | 47 | 0.2618 |
| Group Mean | 9.2 | 815 | | 1.8 | 815 | | 2.0 | 815 | |
| Duncan's LSD$_{0.05}$ | 0.18 | | | 0.08 | | | 0.09 | | |
| CV % | 3.1 | | | 7.5 | | | 7.0 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.
Flagleaf position was rated where 1 = erect, 2 = semi erect, 3 = horizontal, 4 = recurved, and 5 = deflexed

TABLE 3

Morphological characteristics of perennial ryegrasses (*Lolium perenne* L.) cultivars at reproductive maturity, near Connell, WA in 2008.*

| | Flagleaf Length (cm) | | | Bottom Leaf Length (cm) | | | Flagleaf Width (mm) | | | Bottom Leaf Width (mm) | | |
|---|---|---|---|---|---|---|---|---|---|---|---|---|
| Variety | Means | N | prob. | Means | N | prob. | Means | N | prob. | Means | N | prob. |
| 'JS501' | 5.1 | 30 | | 7.9 | 30 | | 3.84 | 30 | | 3.92 | 30 | |
| Yorktown III | 5.7 | 34 | 0.6023 | 6.9 | 34 | 0.5648 | 3.52 | 34 | 0.3306 | 3.68 | 34 | 0.3815 |
| Revenge GLX | 5.9 | 39 | 0.4928 | 7.5 | 39 | 0.7976 | 3.54 | 39 | 0.3484 | 3.52 | 39 | 0.1414 |
| Pinnacle | 6.2 | 32 | 0.3416 | 9.2 | 32 | 0.4686 | 3.88 | 32 | 0.8862 | 3.88 | 32 | 0.8848 |
| Monterey II | 6.2 | 30 | 0.3426 | 8.0 | 30 | 0.9616 | 4.12 | 30 | 0.3839 | 3.97 | 30 | 0.8745 |
| 'APM' | 6.2 | 46 | 0.3056 | 8.0 | 46 | 0.9523 | 3.95 | 44 | 0.7172 | 3.92 | 44 | 0.9873 |
| Accent II | 6.5 | 49 | 0.2208 | 8.7 | 49 | 0.6576 | 3.99 | 48 | 0.6300 | 3.92 | 48 | 0.9794 |
| Brightstar | 6.5 | 48 | 0.2168 | 8.6 | 48 | 0.7081 | 4.04 | 48 | 0.5259 | 3.94 | 48 | 0.9489 |
| 'Intercept TD' | 6.5 | 43 | 0.2118 | 8.9 | 43 | 0.5787 | 4.17 | 42 | 0.2924 | 4.12 | 42 | 0.4713 |
| Caddieshack II | 6.8 | 54 | 0.1263 | 10.5 | 54 | 0.1333 | 4.04 | 54 | 0.5089 | 4.05 | 53 | 0.6226 |
| Top Gun II | 7.0 | 43 | 0.0978 | 8.7 | 43 | 0.6527 | 4.01 | 42 | 0.5952 | 3.88 | 42 | 0.8805 |
| La Quinta | 7.1 | 47 | 0.0836 | 8.8 | 47 | 0.6080 | 3.87 | 47 | 0.9248 | 4.01 | 47 | 0.7400 |
| Pennfine | 7.1 | 28 | 0.0958 | 8.6 | 28 | 0.6899 | 4.15 | 28 | 0.3461 | 3.93 | 28 | 0.9733 |
| Goalkeeper II | 7.1 | 27 | 0.0955 | 9.1 | 27 | 0.5142 | 3.91 | 27 | 0.8210 | 3.97 | 27 | 0.8531 |
| Manhattan II | 7.2 | 58 | 0.0563 | 8.8 | 58 | 0.6238 | 4.25 | 57 | 0.1838 | 4.20 | 57 | 0.2892 |
| Monterey 3 | 7.3 | 45 | 0.0477 | 9.3 | 45 | 0.4324 | 4.31 | 44 | 0.1327 | 4.21 | 44 | 0.2922 |
| Advent | 7.7 | 55 | 0.0207 | 9.0 | 55 | 0.5195 | 4.00 | 54 | 0.6017 | 4.18 | 54 | 0.3377 |
| Linn | 8.2 | 30 | 0.0081 | 10.0 | 30 | 0.2320 | 4.74 | 30 | 0.0058 | 4.75 | 30 | 0.0032 |
| Group Mean | 6.8 | 815 | | 8.7 | 815 | | 4.01 | 806 | | 3.99 | 805 | |
| Duncan's LSD$_{0.05}$ | 1.73 | | | 2.57 | | | 0.48 | | | 0.41 | | |
| CV % | 42.2 | | | 48.2 | | | 20.0 | | | 17.4 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.

TABLE 4

Morphological characteristics of perennial ryegrasses (*Lolium perenne* L.) cultivars at reproductive maturity, near Connell, WA in 2008.*

| | Hue | | | Saturation | | | Intensity | | | Color Grouping | | |
|---|---|---|---|---|---|---|---|---|---|---|---|---|
| Variety | Means | N | prob. | Means | N | prob. | Means | N | prob. | Means | N | prob. |
| 'JS501' | 47.9 | 30 | | 229.6 | 30 | | 26.7 | 30 | | 6.9 | 30 | |
| Goalkeeper II | 50.6 | 27 | 0.2875 | 225.9 | 27 | 0.3857 | 23.3 | 27 | 0.2642 | 7.9 | 27 | 0.0322 |
| La Quinta | 49.1 | 47 | 0.6000 | 225.6 | 47 | 0.3266 | 23.4 | 47 | 0.2516 | 7.7 | 47 | 0.0453 |
| Accent II | 50.3 | 48 | 0.3228 | 228.0 | 48 | 0.6932 | 24.9 | 48 | 0.5287 | 7.4 | 48 | 0.1896 |
| Monterey 3 | 51.1 | 32 | 0.1948 | 229.2 | 32 | 0.9333 | 26.3 | 32 | 0.8774 | 7.2 | 32 | 0.4279 |
| Top Gun II | 51.0 | 42 | 0.1982 | 229.0 | 42 | 0.8898 | 26.3 | 42 | 0.8907 | 7.2 | 42 | 0.4236 |
| Caddieshack II | 49.8 | 51 | 0.4288 | 229.2 | 51 | 0.9228 | 25.9 | 51 | 0.7904 | 7.2 | 51 | 0.4686 |
| Revenge GLX | 52.6 | 39 | 0.0528 | 230.1 | 39 | 0.9079 | 28.4 | 39 | 0.5611 | 6.8 | 39 | 0.8447 |
| 'Intercept TD' | 52.0 | 42 | 0.0937 | 230.7 | 42 | 0.7862 | 30.9 | 42 | 0.1528 | 6.2 | 42 | 0.1500 |
| Brightstar | 53.3 | 48 | 0.0255 | 230.4 | 48 | 0.8442 | 36.5 | 48 | 0.0008 | 5.5 | 48 | 0.0019 |
| Manhattan II | 55.8 | 46 | 0.0011 | 232.4 | 46 | 0.4950 | 37.5 | 46 | 0.0002 | 5.2 | 46 | 0.0002 |
| Pinnacle | 56.2 | 32 | 0.0008 | 232.3 | 32 | 0.5157 | 38.1 | 32 | 0.0002 | 5.1 | 32 | 0.0001 |
| Yorktown III | 59.3 | 34 | 0.0000 | 237.5 | 34 | 0.0590 | 38.6 | 34 | 0.0001 | 5.1 | 34 | 0.0001 |
| Advent | 57.1 | 54 | 0.0001 | 230.6 | 54 | 0.7909 | 40.4 | 54 | 0.0000 | 4.8 | 54 | 0.0000 |
| 'APM' | 58.1 | 45 | 0.0000 | 232.9 | 45 | 0.4161 | 41.2 | 45 | 0.0000 | 4.6 | 45 | 0.0000 |
| Monterey II | 58.5 | 49 | 0.0000 | 228.9 | 49 | 0.8769 | 42.7 | 49 | 0.0000 | 4.5 | 49 | 0.0000 |
| Pennfine | 60.5 | 28 | 0.0000 | 230.5 | 28 | 0.8279 | 45.4 | 28 | 0.0000 | 4.1 | 28 | 0.0000 |
| Linn | 59.1 | 30 | 0.0000 | 214.5 | 30 | 0.0004 | 53.2 | 30 | 0.0000 | 3.1 | 30 | 0.0000 |

TABLE 4-continued

Morphological characteristics of perennial ryegrasses (*Lolium perenne* L.) cultivars at reproductive maturity, near Connell, WA in 2008.*

| Variety | Hue | | | Saturation | | | Intensity | | | Color Grouping | | |
|---|---|---|---|---|---|---|---|---|---|---|---|---|
| | Means | N | prob. | Means | N | prob. | Means | N | prob. | Means | N | prob. |
| Group Mean | 53.8 | 801 | | 229.4 | 801 | | 33.2 | 801 | | 6.0 | 801 | |
| Duncan's LSD$_{0.05}$ | 3.68 | | | 6.22 | | | 4.44 | | | 0.67 | | |
| CV % | 12.9 | | | 4.7 | | | 32.6 | | | 28.4 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.0050 or less would indicate significance at the 5% level of probability.

TABLE 5

Morphological characteristics of perennial ryegrasses (*Lolium perenne* L.) cultivars at reproductive maturity, near Connell, WA in 2008.*

| Variety | Seed Length (mm) | | | Seed Width (mm) | | | Weight/100 Seed | | |
|---|---|---|---|---|---|---|---|---|---|
| | Means | N | prob. | Means | N | prob. | Means | N | prob. |
| 'JS501' | 4.09 | 197 | | 1.19 | 197 | | 0.1030 | 10 | |
| Accent II | 4.34 | 180 | 0.0004 | 1.18 | 180 | 0.4095 | 0.1201 | 10 | 0.5441 |
| Advent | 4.25 | 228 | 0.0120 | 1.16 | 228 | 0.1006 | 0.1350 | 10 | 0.2568 |
| 'APM' | 4.32 | 207 | 0.0005 | 1.15 | 207 | 0.0151 | 0.1380 | 10 | 0.2148 |
| Brightstar | 4.36 | 202 | 0.0001 | 1.20 | 202 | 0.6753 | 0.1223 | 10 | 0.4947 |
| Caddieshack II | 4.41 | 172 | 0.0000 | 1.14 | 172 | 0.0044 | 0.1295 | 10 | 0.3475 |
| Elka | 4.06 | 194 | 0.6455 | 1.14 | 194 | 0.0033 | 0.1062 | 10 | 0.9101 |
| Goalkeeper II | 3.99 | 201 | 0.1466 | 1.07 | 201 | 0.0000 | 0.1391 | 10 | 0.2012 |
| 'Intercept TD' | 4.29 | 197 | 0.0033 | 1.22 | 197 | 0.2103 | 0.1216 | 10 | 0.5098 |
| Linn | 5.10 | 130 | 0.0000 | 1.36 | 130 | 0.0000 | 0.1595 | 10 | 0.0462 |
| La Quinta | 4.31 | 183 | 0.0015 | 1.19 | 183 | 0.8901 | 0.1206 | 10 | 0.5328 |
| Manhattan II | 4.36 | 138 | 0.0004 | 1.19 | 138 | 0.8651 | 0.1392 | 10 | 0.1997 |
| Monterey II | 4.42 | 136 | 0.0000 | 1.20 | 136 | 0.7334 | 0.1047 | 10 | 0.9525 |
| Monterey 3 | 4.14 | 151 | 0.4977 | 1.17 | 151 | 0.2961 | 0.1193 | 10 | 0.5638 |
| Pennfine | 4.59 | 172 | 0.0000 | 1.21 | 172 | 0.3565 | 0.1866 | 10 | 0.0033 |
| Pinnacle | 4.20 | 196 | 0.1132 | 1.11 | 196 | 0.0000 | 0.1313 | 10 | 0.3163 |
| Revenge GLX | 4.01 | 223 | 0.2138 | 1.12 | 223 | 0.0001 | 0.1218 | 10 | 0.5051 |
| Top Gun II | 3.82 | 161 | 0.0002 | 1.11 | 161 | 0.0000 | 0.1140 | 10 | 0.6955 |
| Yorktown III | 4.41 | 184 | 0.0000 | 1.13 | 184 | 0.0009 | 0.1314 | 10 | 0.3141 |
| Group Mean | 4.25 | 3825 | | 1.16 | 3825 | | 0.1282 | 210 | |
| Duncan's LSD$_{0.05}$ | 0.18 | | | 0.05 | | | 0.07 | | |
| CV % | 16.8 | | | 17.3 | | | 48.8 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.

TABLE 6

Morphological characteristics of perennial ryegrasses (*Lolium perenne* L.) cultivars at reproductive maturity, near Connell, WA in 2008.*

| Variety | Days to head emergence |
|---|---|
| 'JS501' | 29 |
| Linn | 22 |
| Pennfine | 24 |
| Pinnacle | 24 |
| 'APM' | 24 |
| Revenge GLX | 24 |
| Manhattan II | 25 |
| Brightstar | 25 |
| Advent | 27 |
| 'Intercept TD' | 29 |
| Accent II | 29 |
| Caddieshack II | 29 |
| La Quinta | 29 |
| Monterey II | 29 |
| Goalkeeper II | 30 |
| Top Gun II | 30 |
| Monterey 3 | 30 |
| Elka | 32 |
| Group Mean | 27 |
| Duncan's LSD$_{0.05}$ | NS |
| CV % | 13.4 |

Days to head emergence were tabulated as days from May 1st. For example, June $1^{st}$ = 32.

The following Tables 7-12 identify morphological characteristics of the new perennial ryegrass 'Jacklin 501' and other perennial ryegrass cultivars at reproductive maturity taken in 2008 from the Post Falls, Id. trial.

TABLE 7

Morphological characteristics of perennial ryegrasses (*Lolium perenne* L.) cultivars at reproductive maturity, near Rathdrum, Idaho in 2008.*

| Variety | Flagleaf Height (cm) | | | Sheath Length (cm) | | | Spike Length (cm) | | | Plant Height (cm) | | |
|---|---|---|---|---|---|---|---|---|---|---|---|---|
| | Means | N | prob. | Means | N | prob. | Means | N | prob. | Means | N | prob. |
| 'JS501' | 30.6 | 58 | | 8.7 | 58 | | 12.3 | 58 | | 52.2 | 58 | |
| Elka | 20.7 | 3 | 0.0007 | 7.5 | 3 | 0.1789 | 13.3 | 3 | 0.4977 | 38.7 | 3 | 0.0002 |
| Revenge GLX | 28.2 | 58 | 0.0110 | 8.6 | 58 | 0.7057 | 11.4 | 58 | 0.0485 | 48.4 | 58 | 0.0010 |
| Goalkeeper II | 27.9 | 58 | 0.0036 | 9.0 | 58 | 0.3740 | 13.0 | 58 | 0.1193 | 50.0 | 58 | 0.0551 |
| Monterey II | 28.9 | 58 | 0.0770 | 9.7 | 58 | 0.0003 | 13.6 | 58 | 0.0051 | 50.5 | 58 | 0.1235 |
| Monterey 3 | 30.6 | 58 | 0.9241 | 9.1 | 58 | 0.2032 | 12.9 | 58 | 0.2380 | 50.8 | 58 | 0.2183 |
| Top Gun II | 30.4 | 58 | 0.8714 | 9.7 | 58 | 0.0004 | 13.1 | 58 | 0.0968 | 50.9 | 58 | 0.2673 |
| 'Intercept TD' | 27.5 | 58 | 0.0008 | 8.4 | 58 | 0.2304 | 13.7 | 58 | 0.0017 | 51.7 | 58 | 0.6596 |
| Accent II | 31.4 | 68 | 0.3252 | 9.3 | 68 | 0.0224 | 12.7 | 68 | 0.3687 | 53.2 | 68 | 0.3910 |
| Pinnacle | 29.5 | 58 | 0.2580 | 9.5 | 58 | 0.0075 | 14.0 | 58 | 0.0002 | 53.6 | 58 | 0.2374 |
| La Quinta | 32.4 | 58 | 0.0391 | 8.5 | 58 | 0.4502 | 12.1 | 58 | 0.6715 | 53.7 | 58 | 0.2095 |
| Pennfine | 29.9 | 58 | 0.4657 | 10.4 | 58 | 0.0000 | 14.3 | 58 | 0.0000 | 54.0 | 58 | 0.1224 |
| Advent | 28.9 | 68 | 0.0645 | 9.9 | 68 | 0.0000 | 15.8 | 68 | 0.0000 | 54.3 | 68 | 0.0605 |
| Brightstar | 32.2 | 68 | 0.0643 | 9.7 | 68 | 0.0006 | 13.1 | 68 | 0.0727 | 55.7 | 68 | 0.0018 |
| Linn | 30.6 | 58 | 0.9287 | 11.0 | 58 | 0.0000 | 13.5 | 58 | 0.0077 | 55.8 | 58 | 0.0017 |
| Manhattan II | 30.1 | 58 | 0.6218 | 9.8 | 58 | 0.0002 | 14.3 | 58 | 0.0000 | 57.0 | 58 | 0.0000 |
| Caddieshack II | 35.6 | 68 | 0.0000 | 10.9 | 68 | 0.0000 | 15.3 | 68 | 0.0000 | 59.9 | 68 | 0.0000 |
| 'APM' | 38.1 | 68 | 0.0000 | 11.2 | 68 | 0.0000 | 15.7 | 68 | 0.0000 | 60.8 | 68 | 0.0000 |
| Group mean | 30.8 | 1155 | | 9.5 | 1155 | | 13.5 | 1155 | | 53.4 | 1155 | |
| Duncan's LSD$_{0.05}$ | 3.04 | | | 0.95 | | | 1.52 | | | 3.85 | | |
| CV % | 17.9 | | | 18.2 | | | 20.1 | | | 13.1 | | |

*Data were analyzed with ANOVA and means were separated with LSD using pair-wise comparisons, based on individual degrees of freedom.

Prob. = Probability that the variety mean is not significantly different from the variety listed at the top of the table. For example, a value of 0.050 or less would indicate significance at the 5% level of probability.

TABLE 8

Morphological characteristics of perennial ryegrasses (*Lolium perenne* L.) cultivars at reproductive maturity, near Rathdrum, Idaho in 2008.*

| Variety | Flagleaf Position | | | Flagleaf Categories | | | | | |
|---|---|---|---|---|---|---|---|---|---|
| | | | | % Erect | | | % Semi erect | | |
| | Means | N | prob. | Means | N | prob. | Means | N | prob. |
| 'JS501' | 2.0 | 67 | | 10.4 | 67 | | 84 | 67 | |
| Monterey 3 | 2.7 | 74 | 0.0000 | 19.4 | 36 | 0.2290 | 81 | 36 | 0.7411 |
| Caddieshack II | 2.2 | 79 | 0.1310 | 15.2 | 79 | 0.4301 | 65 | 79 | 0.0099 |
| Brightstar | 2.2 | 80 | 0.2335 | 12.5 | 80 | 0.7320 | 73 | 80 | 0.1313 |
| 'APM' | 2.1 | 55 | 0.3374 | 9.1 | 55 | 0.8367 | 76 | 55 | 0.3709 |
| Linn | 2.1 | 49 | 0.3628 | 24.5 | 49 | 0.0391 | 61 | 49 | 0.0074 |
| Pennfine | 2.1 | 71 | 0.7451 | 9.9 | 71 | 0.9239 | 80 | 71 | 0.6620 |
| Manhattan II | 2.0 | 74 | 0.8390 | 20.3 | 74 | 0.1076 | 65 | 74 | 0.0124 |
| Advent | 2.0 | 26 | 0.8916 | 23.1 | 26 | 0.1310 | 62 | 26 | 0.0315 |
| La Quinta | 2.0 | 78 | 0.9314 | 12.8 | 78 | 0.6938 | 77 | 78 | 0.3672 |
| Goalkeeper II | 2.0 | 78 | 0.9046 | 11.5 | 78 | 0.8564 | 82 | 78 | 0.8358 |
| Revenge GLX | 2.0 | 71 | 0.9067 | 9.9 | 71 | 0.9239 | 85 | 71 | 0.9025 |
| Accent II | 2.0 | 82 | 0.8257 | 15.9 | 82 | 0.3643 | 74 | 82 | 0.2081 |
| Top Gun II | 2.0 | 81 | 0.8252 | 21.0 | 81 | 0.0779 | 67 | 81 | 0.0210 |
| 'Intercept TD' | 1.9 | 75 | 0.3335 | 22.7 | 75 | 0.0447 | 71 | 75 | 0.0833 |
| Pinnacle | 1.8 | 68 | 0.1700 | 23.5 | 68 | 0.0358 | 72 | 68 | 0.1312 |
| Monterey II | 1.8 | 36 | 0.1756 | 4.1 | 74 | 0.2948 | 62 | 74 | 0.0042 |
| Group Mean | 2.1 | 1262 | | 15.7 | 1262 | | 73 | 1262 | |
| Duncan's LSD$_{0.05}$ | 33.40 | | | 16.2 | | | 20 | | |
| CV % | 37.2 | | | 23.2 | | | 6 | | |

| Variety | Flagleaf Categories | | | | | | | | |
|---|---|---|---|---|---|---|---|---|---|
| | % Horizontal | | | % Recurved | | | % Deflexed | | |
| | Means | N | prob. | Means | N | prob. | Means | N | prob. |
| 'JS501' | 0.0 | 67 | | 6.0 | 67 | | 0 | 67 | |
| Monterey 3 | 0.0 | 36 | 1.0000 | 0.0 | 36 | 0.2115 | 0 | 36 | 1.0000 |
| Caddieshack II | 6.3 | 79 | 0.0557 | 12.7 | 79 | 0.0817 | 1.3 | 79 | 0.5517 |
| Brightstar | 5.0 | 80 | 0.1294 | 6.3 | 80 | 0.9417 | 3.8 | 80 | 0.0771 |
| 'APM' | 9.1 | 55 | 0.0122 | 1.8 | 55 | 0.3237 | 3.6 | 55 | 0.1187 |
| Linn | 2.0 | 49 | 0.5854 | 0.0 | 49 | 0.1696 | 12.2 | 49 | 0.0000 |
| Pennfine | 4.2 | 71 | 0.2127 | 5.6 | 71 | 0.9319 | 0.0 | 71 | 1.0000 |
| Manhattan II | 5.4 | 74 | 0.1074 | 9.5 | 74 | 0.3708 | 0.0 | 74 | 1.0000 |

TABLE 8-continued

Morphological characteristics of perennial ryegrasses (*Lolium perenne* L.) cultivars at reproductive maturity, near Rathdrum, Idaho in 2008.*

| | | | | | | | | | |
|---|---|---|---|---|---|---|---|---|---|
| Advent | 3.8 | 26 | 0.4029 | 11.5 | 26 | 0.2973 | 0.0 | 26 | 1.0000 |
| La Quinta | 5.1 | 78 | 0.1220 | 5.1 | 78 | 0.8269 | 0.0 | 78 | 1.0000 |
| Goalkeeper II | 2.6 | 78 | 0.4392 | 2.6 | 78 | 0.3765 | 1.3 | 78 | 0.5478 |
| Revenge GLX | 1.4 | 71 | 0.6777 | 4.2 | 71 | 0.6577 | 0.0 | 71 | 1.0000 |
| Accent II | 4.9 | 82 | 0.1368 | 4.9 | 82 | 0.7742 | 0.0 | 82 | 1.0000 |
| Top Gun II | 4.9 | 81 | 0.1331 | 7.4 | 81 | 0.7066 | 0.0 | 81 | 1.0000 |
| 'Intercept TD' | 2.7 | 75 | 0.4254 | 2.7 | 75 | 0.3954 | 1.3 | 75 | 0.5356 |
| Pinnacle | 1.5 | 68 | 0.6677 | 2.9 | 68 | 0.4466 | 0.0 | 68 | 1.0000 |
| Monterey II | 6.8 | 74 | 0.0442 | 17.6 | 74 | 0.0030 | 9.5 | 74 | 0.0000 |
| Group Mean | 4.1 | 1262 | | 5.8 | 1262 | | 1.7 | 1262 | |
| Duncan's LSD$_{0.05}$ | 8.9 | | | 10.3 | | | 5.7 | | |
| CV % | 48.3 | | | 40.4 | | | 75.1 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.
Flagleaf position was rated where 1 = erect, 2 = semi erect, 3 = horizontal, 4 = recurved, and 5 = deflexed

TABLE 9

Morphological characteristics of perennial ryegrasses (*Lolium perenne* L.) cultivars at reproductive maturity, near Rathdrum, Idaho in 2008.*

| | Flagleaf Length (cm) | | | Bottom Leaf Length (cm) | | | Flagleaf Width (mm) | | | Bottom Leaf Width (mm) | | |
|---|---|---|---|---|---|---|---|---|---|---|---|---|
| Variety | Means | N | prob. | Means | N | prob. | Means | N | prob. | Means | N | prob. |
| 'JS501' | 8.2 | 67 | | 9.8 | 67 | | 3.97 | 62 | | 3.56 | 63 | |
| Accent II | 8.4 | 82 | 0.5054 | 10.5 | 82 | 0.1088 | 3.30 | 79 | 0.0000 | 3.31 | 79 | 0.0441 |
| Pinnacle | 8.5 | 68 | 0.4438 | 10.6 | 68 | 0.0677 | 3.28 | 64 | 0.0000 | 3.00 | 65 | 0.0000 |
| Brightstar | 8.7 | 80 | 0.1667 | 11.0 | 80 | 0.0057 | 3.24 | 77 | 0.0000 | 3.21 | 78 | 0.0046 |
| Monterey II | 8.9 | 36 | 0.0000 | 10.7 | 36 | 0.1042 | 3.83 | 33 | 0.4237 | 3.77 | 31 | 0.1821 |
| Revenge GLX | 8.9 | 71 | 0.0997 | 10.4 | 71 | 0.1911 | 3.25 | 69 | 0.0000 | 3.00 | 69 | 0.0000 |
| 'APM' | 9.0 | 55 | 0.0827 | 10.5 | 55 | 0.1163 | 3.37 | 50 | 0.0001 | 3.58 | 48 | 0.8484 |
| Advent | 9.0 | 26 | 0.1627 | 10.8 | 26 | 0.0964 | 3.93 | 26 | 0.8598 | 3.31 | 26 | 0.1417 |
| La Quinta | 9.2 | 78 | 0.0128 | 11.1 | 78 | 0.0027 | 3.38 | 75 | 0.0000 | 3.16 | 74 | 0.0018 |
| 'Intercept TD' | 9.3 | 75 | 0.0073 | 11.3 | 75 | 0.0005 | 3.77 | 73 | 0.1566 | 3.52 | 74 | 0.7570 |
| Goalkeeper II | 9.5 | 78 | 0.0013 | 11.6 | 78 | 0.0000 | 3.42 | 74 | 0.0001 | 3.38 | 74 | 0.1577 |
| Pennfine | 9.6 | 71 | 0.0010 | 10.5 | 71 | 0.1006 | 3.34 | 68 | 0.0000 | 3.05 | 68 | 0.0001 |
| Top Gun II | 9.6 | 81 | 0.0006 | 11.8 | 81 | 0.0000 | 3.53 | 78 | 0.0018 | 3.51 | 78 | 0.6853 |
| Linn | 9.6 | 49 | 0.0020 | 11.8 | 49 | 0.0000 | 3.63 | 49 | 0.0328 | 3.65 | 49 | 0.4885 |
| Caddieshack II | 10.3 | 79 | 0.0000 | 12.7 | 79 | 0.0000 | 3.76 | 78 | 0.1403 | 3.64 | 78 | 0.5083 |
| Monterey 3 | 10.6 | 74 | 0.1868 | 12.8 | 74 | 0.0000 | 3.58 | 74 | 0.0057 | 3.53 | 73 | 0.8526 |
| Manhattan II | 10.6 | 74 | 0.0000 | 12.2 | 74 | 0.0000 | 3.76 | 71 | 0.1362 | 3.56 | 71 | 0.9527 |
| Group Mean | 9.3 | 1262 | | 11.2 | 1262 | | 3.51 | 1216 | | 3.38 | 1214 | |
| Duncan's LSD$_{0.05}$ | 1.11 | | | 1.18 | | | 0.37 | | | 0.33 | | |
| CV % | 27.7 | | | 24.6 | | | 78.3 | | | 22.5 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.

TABLE 10

Morphological characteristics of perennial ryegrasses (*Lolium perenne* L.) cultivars at reproductive maturity, near Rathdrum, Idaho in 2008.*

| | Leaf Color | | | | | | | | | | | |
|---|---|---|---|---|---|---|---|---|---|---|---|---|
| | Hue | | | Saturation | | | Intensity | | | Color Grouping | | |
| Variety | Means | N | prob. | Means | N | prob. | Means | N | prob. | Means | N | prob. |
| 'JS501' | 53.4 | 82 | | 228.7 | 82 | | 28.4 | 82 | | 6.8 | 82 | |
| La Quinta | 50.0 | 73 | 0.0006 | 223.7 | 73 | 0.0033 | 21.9 | 73 | 0.0000 | 8.2 | 73 | 0.0000 |
| Goalkeeper II | 49.7 | 74 | 0.0002 | 225.8 | 74 | 0.0925 | 25.0 | 74 | 0.0120 | 7.6 | 74 | 0.0000 |
| Monterey 3 | 49.5 | 74 | 0.0001 | 226.4 | 74 | 0.1863 | 25.9 | 74 | 0.0710 | 7.4 | 74 | 0.0019 |
| Accent II | 48.9 | 79 | 0.0000 | 229.5 | 79 | 0.6302 | 25.5 | 79 | 0.0314 | 7.2 | 79 | 0.0307 |
| Top Gun II | 52.3 | 75 | 0.2903 | 229.4 | 75 | 0.6759 | 26.8 | 75 | 0.2381 | 7.2 | 75 | 0.0402 |
| Caddieshack II | 50.7 | 91 | 0.0043 | 228.3 | 91 | 0.8210 | 26.8 | 91 | 0.2236 | 7.2 | 91 | 0.0402 |
| Revenge GLX | 53.3 | 69 | 0.9260 | 230.6 | 69 | 0.2522 | 29.2 | 69 | 0.5247 | 6.8 | 69 | 0.8436 |
| 'Intercept TD' | 52.1 | 73 | 0.2114 | 232.0 | 73 | 0.0500 | 31.0 | 73 | 0.0492 | 6.2 | 73 | 0.0129 |
| Brightstar | 54.7 | 77 | 0.1693 | 228.4 | 77 | 0.8534 | 35.6 | 77 | 0.0000 | 5.6 | 77 | 0.0000 |
| Manhattan II | 55.3 | 74 | 0.0447 | 230.3 | 74 | 0.3226 | 37.4 | 74 | 0.0000 | 5.1 | 74 | 0.0000 |

TABLE 10-continued

Morphological characteristics of perennial ryegrasses (*Lolium perenne* L.) cultivars at reproductive maturity, near Rathdrum, Idaho in 2008.*

| | Leaf Color | | | | | | | | | | | |
|---|---|---|---|---|---|---|---|---|---|---|---|---|
| | Hue | | | Saturation | | | Intensity | | | Color Grouping | | |
| Variety | Means | N | prob. | Means | N | prob. | Means | N | prob. | Means | N | prob. |
| Pinnacle | 56.0 | 64 | 0.0100 | 228.7 | 64 | 0.9990 | 38.6 | 64 | 0.0000 | 5.1 | 64 | 0.0000 |
| Advent | 58.8 | 26 | 0.0001 | 231.3 | 26 | 0.2695 | 42.3 | 26 | 0.0000 | 4.5 | 26 | 0.0000 |
| Monterey II | 58.4 | 34 | 0.0000 | 230.6 | 34 | 0.3677 | 42.7 | 34 | 0.0000 | 4.4 | 34 | 0.0000 |
| 'APM' | 58.8 | 50 | 0.0000 | 229.5 | 50 | 0.6552 | 43.1 | 50 | 0.0000 | 4.4 | 50 | 0.0000 |
| Pennfine | 58.5 | 66 | 0.0000 | 225.3 | 66 | 0.0568 | 45.2 | 66 | 0.0000 | 4.1 | 66 | 0.0000 |
| Linn | 58.6 | 48 | 0.0000 | 213.6 | 48 | 0.0000 | 53.7 | 48 | 0.0000 | 3.2 | 48 | 0.0000 |
| Group Mean | 53.2 | 1221 | | 227.7 | 1221 | | 32.1 | 1221 | | 6.3 | 1221 | |
| Duncan's LSD$_{0.05}$ | 2.79 | | | 4.78 | | | 3.79 | | | 0.58 | | |
| CV % | 12.9 | | | 4.8 | | | 35.8 | | | 29.3 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.
Color Grouping is the visual ranking of the plants using a 1-9 scale where 9 = darkest.

TABLE 11

Morphological characteristics of perennial ryegrasses (*Lolium perenne* L.) cultivars at reproductive maturity, near Rathdrum, Idaho in 2008.*

| | Seed Length (mm) | | | Seed Width (mm) | | | Weight/100 Seed | | |
|---|---|---|---|---|---|---|---|---|---|
| Variety | Means | N | prob. | Means | N | prob. | Means | N | prob. |
| 'JS501' | 4.88 | 192 | | 1.32 | 192 | | 0.1257 | 10 | |
| Linn | 5.59 | 175 | 0.0000 | 1.39 | 175 | 0.0001 | 0.1900 | 5 | 0.0692 |
| Pennfine | 5.38 | 197 | 0.0000 | 1.27 | 197 | 0.0013 | 0.1247 | 10 | 0.9714 |
| 'APM' | 5.35 | 148 | 0.0000 | 1.25 | 148 | 0.0002 | 0.1258 | 10 | 0.9992 |
| Advent | 5.27 | 184 | 0.0000 | 1.26 | 184 | 0.0002 | 0.1360 | 10 | 0.7202 |
| Caddieshack II | 5.25 | 137 | 0.0000 | 1.26 | 137 | 0.0012 | 0.1416 | 10 | 0.5814 |
| Brightstar | 5.20 | 178 | 0.0000 | 1.30 | 178 | 0.2594 | 0.0937 | 10 | 0.2662 |
| Monterey II | 5.17 | 211 | 0.0000 | 1.24 | 211 | 0.0000 | 0.1384 | 10 | 0.6605 |
| Manhattan II | 5.09 | 189 | 0.0027 | 1.23 | 189 | 0.0000 | 0.1297 | 10 | 0.8910 |
| Pinnacle | 5.02 | 210 | 0.0353 | 1.21 | 210 | 0.0000 | 0.1384 | 10 | 0.6600 |
| Goalkeeper II | 4.88 | 155 | 0.9694 | 1.23 | 155 | 0.0000 | 0.1169 | 10 | 0.7596 |
| La Quinta | 4.83 | 186 | 0.5156 | 1.19 | 186 | 0.0000 | 0.1185 | 10 | 0.8001 |
| Accent II | 4.75 | 203 | 0.0631 | 1.20 | 203 | 0.0000 | 0.1213 | 10 | 0.8784 |
| Revenge GLX | 4.68 | 195 | 0.0041 | 1.18 | 195 | 0.0000 | 0.1960 | 10 | 0.0155 |
| Top Gun II | 4.65 | 238 | 0.0007 | 1.17 | 238 | 0.0000 | 0.1296 | 10 | 0.8938 |
| Monterey 3 | 4.60 | 264 | 0.0000 | 1.15 | 264 | 0.0000 | 0.1073 | 10 | 0.5209 |
| 'Intercept TD' | 4.49 | 167 | 0.0000 | 1.17 | 167 | 0.0000 | 0.1013 | 10 | 0.3966 |
| Group Mean | 4.96 | 3587 | | 1.23 | 3587 | | 0.1277 | 185 | |
| Duncan's LSD$_{0.05}$ | 0.18 | | | 0.04 | | | 0.07 | | |
| CV % | 15.1 | | | 15.0 | | | 51.2 | | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.

TABLE 12

Morphological characteristics of perennial ryegrasses (*Lolium perenne* L.) cultivars at reproductive maturity, near Rathdrum, Idaho in 2008.*

| Variety | Days to head emergence |
|---|---|
| 'JS501' | 43 |
| Linn | 36 |
| Pennfine | 38 |
| Pinnacle | 38 |
| 'APM' | 38 |
| Revenge GLX | 41 |
| Manhattan II | 41 |
| Brightstar | 42 |
| Advent | 43 |
| 'Intercept TD' | 43 |
| Accent II | 43 |
| Caddieshack II | 43 |
| La Quinta | 44 |
| Monterey II | 44 |
| Goalkeeper II | 44 |
| Top Gun II | 44 |
| Monterey 3 | 44 |
| Elka | 45 |
| Group Mean | 42 |
| LSD 0.05 | NS |
| CV % | 8.4 |

Days to head emergence were tabulated as days from May 1st. For example, June $1^{st}$ = 32. Plant heading was about 1 week later in heading than normal but they sped up with many plants having pollen before they panicles were completely extended.

B. Turf Trials

'JS501' has been evaluated in turf trials in Rathdrum, Id., Poolesville, Md., and Carlisle, Ohio, and data from these trials is presented in the following Table 13-15, respectively. The turf trials were all planted in August of 2007, and varied in size with many entries (especially those from single plant selections not being replicated), but a core group of about 30 entries being replicated 2, 3 or 4 times at each location.

The Rathdrum, Id. location has the highest management regime and is maintained at 1¼" inches mowed height, fertilized 3 times per year, watered to prevent stress, and pesticides are applied as needed. Plants of the new perennial ryegrass 'JS501' performed best in trials in Rathdrum, Id., where it was mid-ranked (statistically (p=0.05) comparable to the top entries in the trial) for turf quality, turf density, tolerance to pink snow mold, and spring greenup, but was inferior to the top entries in the trial for turf color, seed vigor and establishment. In this trial, based on a 1 to 9 visual scale where 1=dead or worst performance and 9=the best performance, 'Intercept TD' rated 6.0 for turf quality, 6.8 for turf density, 7.0 for pink snow mold tolerance (caused by *Microdochium nivale*), 5.5 for spring greenup, 6.8 for turf color, 3.5 for seed vigor, and 6.5 for seedling establishment rate. Based on two ratings for pink snow mold resistance in the Rathdrum, Id. trial, 'JS501' was the highest ranked among the entries in the trial. In trials in Rathdrum, Id., 'JS501' compared similarly to Top Gun II on seed vigor, turf density, turf color, and spring greenup, but was inferior on establishment. Top Gun II rated a 6.2 in turf quality, 5.3 in seed vigor, 8.0 in establishment rate, 7.3 in turf color, 3.8 in tolerance to pink snow mold, and 6.5 in turf density. Linn rated a 2.9 in quality, 2.5 in seed vigor, 5.0 in establishment rate, 3.0 in spring greenup, 3.0 in color, 2.0 in pink snow mold resistance, and 2.5 in density.

The Maryland trial is low management and mowed intermittently during the growing season at 3" inches mowed height and does not receive supplemental irrigation. During 2008 the Maryland turf went dormant during the hottest months of summer. In this trial, 'JS501' was comparable to Top Gun II in establishment and net blotch, but was inferior on turf quality, turf color, spring greenup and leaf spot resistance. 'JS501' had similar turf quality and establishment to Accent and Radiant. In this trial, 'JS501' rated a 2.6 in quality, 3.0 in spring greenup, 2.5 in leaf spot, 2.5 in net blotch, 5.8 in turf color, and 2.0 in establishment. In this trial, Accent II rated a 4.2 in quality, 6.0 in spring greenup, 5.0 in leaf spot, 2.3 in net blotch, 7.0 in turf color, and 3.3 in establishment. In this trial, Linn rated a 1.6 in quality, 3.0 in spring greenup, 1.0 in leaf spot, 1.0 in net blotch, 1.5 in turf color, and 2.0 in establishment.

The Ohio trial is also low management, but does not go dormant during the summer. 'JS501' was mid-ranked in the trial and comparable to Top Gun II in spring greenup and turf color. 'JS501' rated a 3.9 in quality, 6.0 in spring greenup, 2.8 in rust resistance, 6.5 in color, and 3.0 on establishment. In comparison, Top Gun II rated a 5.9 in quality, 6.5 in spring greenup, 5.5 in rust resistance, 5.0 in color, and 2.0 in establishment. In this trial, Linn rated a 1.7 in quality, 2.0 in spring greenup, 1.0 in rust resistance, 1.0 in color, and 2.0 in establishment.

TABLE 13

2007 perennial ryegrass turf trial at Rathdrum, ID. Results through September, 2008.

| Variety | N | Seed vigor | | Establishment August 2007 | | Spring greenup April 2008 | | Color | | Pink Snow Mold | | Density | | Quality | |
|---|---|---|---|---|---|---|---|---|---|---|---|---|---|---|---|
| | | Avg. | prob. | Avg. | prob. | Avg. | prob. | Avg. | prob. | Avg. | prob. | Avg. | prob. | Avg. | prob. |
| 'JS501' | 2 | 3.5 | | 6.5 | | 5.5 | | 6.8 | | 7.0 | | 6.8 | | 6.0 | |
| GL-2 | 2 | 5.5 | 0.0294 | 8.0 | 0.0340 | 4.5 | 0.3000 | 7.8 | 0.0401 | 3.5 | 0.0023 | 7.8 | 0.0409 | 6.8 | 0.0479 |
| Revenge GLX | 2 | 4.3 | 0.4030 | 7.5 | 0.1516 | 5.0 | 0.6026 | 7.8 | 0.0401 | 4.0 | 0.0082 | 7.8 | 0.0409 | 6.6 | 0.1460 |
| Accent II | 2 | 5.0 | 0.0983 | 8.5 | 0.0055 | 6.0 | 0.6026 | 7.5 | 0.1198 | 4.3 | 0.0147 | 6.8 | 1.0000 | 6.2 | 0.5817 |
| Top Gun II | 2 | 5.3 | 0.0551 | 8.0 | 0.0340 | 5.0 | 0.6026 | 7.3 | 0.2960 | 3.8 | 0.0044 | 6.5 | 0.6011 | 6.2 | 0.5817 |
| Radiant | 2 | 1.8 | 0.0551 | 3.5 | 0.0001 | 5.5 | 1.0000 | 7.3 | 0.2960 | 6.3 | 0.4922 | 7.0 | 0.6011 | 6.1 | 0.8541 |
| Monterey 3 | 2 | 5.0 | 0.0983 | 6.5 | 1.0000 | 3.5 | 0.0417 | 7.5 | 0.1198 | 3.5 | 0.0023 | 6.8 | 1.0000 | 5.8 | 0.5817 |
| 'Intercept TD' | 2 | 3.8 | 0.7797 | 7.0 | 0.4695 | 4.0 | 0.1228 | 6.3 | 0.2960 | 3.0 | 0.0006 | 6.8 | 1.0000 | 5.6 | 0.3600 |
| Accent | 2 | 6.3 | 0.0034 | 8.0 | 0.0340 | 4.0 | 0.1228 | 5.5 | 0.0113 | 2.8 | 0.0003 | 6.0 | 0.1213 | 5.1 | 0.0316 |
| Linn | 1 | 2.5 | 0.3629 | 5.0 | 0.0808 | 3.0 | 0.0379 | 3.0 | 0.0000 | 2.0 | 0.0005 | 2.5 | 0.0000 | 2.9 | 0.0000 |
| Group Mean | | 4.4 | | 7.3 | | 4.5 | | 7.1 | | 4.0 | | 6.8 | | 5.9 | |
| Number of entries | 78 | 34 | | 34 | | 34.0 | | 34 | | 34 | | 34 | | 34 | |
| Overall high | | 6.8 | | 9.0 | | 6.0 | | 8.0 | | 7.0 | | 7.8 | | 6.8 | |
| Overall low | | 1.8 | | 3.5 | | 1.5 | | 3.0 | | 1.8 | | 2.5 | | 2.9 | |
| Duncan's $LSD_{0.05}$ | | 2.12 | | 1.63 | | 2.3 | | 1.13 | | 2.58 | | 1.13 | | 0.92 | |
| CV % | | 27.4 | | 16.2 | | 26.7 | | 14.1 | | 35.4 | | 11.2 | | 11.5 | |

*Data were analyzed with ANOVA and means were separated with LSD using pair-wise comparisons, based on individual degrees of freedom.

Prob. = Probability that the variety mean is not significantly different from the variety listed at the top of the table. For example, a value of 0.050 or less would indicate significance at the 5% level of probability.

Seed vigor, color, pink snow mold and density were rated twice, establishment and spring greenup once, and quality seven times.

TABLE 14

2007 perennial ryegrass turf trial at Poolesville, Maryland. Results through November, 2008.

| | | Establishment | | Color | | Net blotch | | Leaf spot | | Spring greenup | | Quality | |
| | | November | | | | July | | November | | April | | | |
| Variety | N | 2007 | prob. | Avg. | prob. | 2008 | prob. | 2008 | prob. | 2008 | prob. | Avg. | prob. |
|---|---|---|---|---|---|---|---|---|---|---|---|---|---|
| 'JS501' | 2 | 2.0 | | 5.8 | | 2.5 | | 2.5 | | 3.0 | | 2.6 | |
| Monterey 3 | 2 | 2.7 | 0.4516 | 5.3 | 0.4968 | 4.0 | 0.1784 | 6.0 | 0.0004 | 5.7 | 0.0065 | 4.6 | 0.0027 |
| GL-2 | 4 | 3.0 | 0.2354 | 5.9 | 0.8296 | 3.8 | 0.2365 | 6.3 | 0.0001 | 5.3 | 0.0150 | 4.5 | 0.0023 |
| Revenge GLX | 3 | 2.3 | 0.7062 | 5.8 | 0.8917 | 4.0 | 0.1784 | 6.7 | 0.0000 | 4.7 | 0.0841 | 4.3 | 0.0099 |
| Accent II | 3 | 3.3 | 0.1345 | 7.0 | 0.0442 | 2.3 | 0.8804 | 5.0 | 0.0097 | 6.0 | 0.0024 | 4.2 | 0.0121 |
| Top Gun II | 3 | 3.0 | 0.2600 | 6.7 | 0.1374 | 2.3 | 0.8804 | 5.3 | 0.0036 | 5.3 | 0.0167 | 4.2 | 0.0148 |
| 'Intercept TD' | 3 | 2.7 | 0.4516 | 4.8 | 0.1374 | 3.0 | 0.6519 | 2.7 | 0.8597 | 4.0 | 0.2967 | 3.0 | 0.5156 |
| Accent | 3 | 2.7 | 0.4516 | 2.7 | 0.0000 | 2.0 | 0.6519 | 2.0 | 0.5964 | 4.7 | 0.0841 | 2.6 | 0.9694 |
| Radiant | 3 | 1.7 | 0.7062 | 8.2 | 0.0002 | 1.3 | 0.2940 | 3.0 | 0.5964 | 2.7 | 0.7270 | 2.3 | 0.6188 |
| Linn | 1 | 2.0 | 1.0000 | 1.5 | 0.0000 | 1.0 | 0.3145 | 1.0 | 0.2382 | 3.0 | 1.0000 | 1.6 | 0.2015 |
| Group Mean | | 2.8 | | 6.0 | | 3.2 | | 4.5 | | 4.8 | | 3.8 | |
| Number of entries | 115 | 48 | | 48 | | 48 | | 48 | | 48 | | 48 | |
| Overall high | | 6.0 | | 8.2 | | 7.0 | | 7.3 | | 8.0 | | 5.4 | |
| Overall low | | 1.0 | | 1.5 | | 1.0 | | 1.0 | | 2.7 | | 1.6 | |
| Duncan's LSD 0.05 | | 2.5 | | 1.7 | | 3.1 | | 2.7 | | 2.7 | | 1.8 | |
| CV % | | 38.6 | | 29.2 | | 42.0 | | 39.7 | | 23.5 | | 25.2 | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.
Color was rated twice, establishment, spring greenup, net blotch and leaf spot once, and quality seven times.

TABLE 15

2007 perennial ryegrass turf trial at New Carlisle, Ohio. Results through November, 2008.

| | | Establishment | | Color | | Rust | | Spring greenup | | Quality | |
| | | December | | May | | | | May | | | |
| Variety | N | 2007 | prob. | 2008 | prob. | Avg. | prob. | 2008 | prob. | Avg. | prob. |
|---|---|---|---|---|---|---|---|---|---|---|---|
| 'JS501' | 2 | 3.0 | | 6.5 | | 2.8 | | 6.0 | | 3.9 | |
| Accent II | 2 | 5.5 | 0.0084 | 4.0 | 0.0096 | 6.0 | 0.0000 | 6.5 | 0.4225 | 6.0 | 0.0000 |
| Monterey 3 | 2 | 5.5 | 0.0084 | 5.0 | 0.1097 | 6.0 | 0.0000 | 5.5 | 0.4225 | 5.9 | 0.0001 |
| Top Gun II | 2 | 5.0 | 0.0326 | 5.0 | 0.1097 | 5.5 | 0.0003 | 6.5 | 0.4225 | 5.9 | 0.0001 |
| GL-2 | 2 | 5.5 | 0.0084 | 3.5 | 0.0023 | 5.0 | 0.0027 | 6.0 | 1.0000 | 5.1 | 0.0065 |
| 'Intercept TD' | 2 | 4.0 | 0.2760 | 4.0 | 0.0319 | 3.3 | 0.4840 | 5.5 | 0.4225 | 4.3 | 0.3464 |
| Accent | 2 | 3.0 | 1.0000 | 1.0 | 0.0000 | 2.0 | 0.2954 | 4.0 | 0.0023 | 3.2 | 0.1604 |
| Radiant | 2 | 1.5 | 0.1050 | 8.0 | 0.1891 | 1.3 | 0.0398 | 3.0 | 0.0000 | 2.1 | 0.0004 |
| Linn | 1 | 2.0 | 0.3727 | 1.0 | 0.0000 | 1.0 | 0.0497 | 2.0 | 0.0000 | 1.7 | 0.0003 |
| Group Mean | | 4.8 | | 5.9 | | 4.6 | | 6.4 | | 5.2 | |
| Number of entries | 222 | 177 | | 177 | | 177 | | 177 | | 177 | |
| Overall high | | 8 | | 9.0 | | 7.5 | | 9.0 | | 7.9 | |
| Overall low | | 1.5 | | 1.0 | | 1.0 | | 2.0 | | 1.7 | |
| Duncan's LSD 0.05 | | 2.8 | | 2.8 | | 2.2 | | 1.9 | | 1.4 | |
| CV % | | 27.4 | | 35.4 | | 27.7 | | 18.6 | | 18.3 | |

*Data were analyzed with ANOVA and means were separated with LSD using pair-wise comparisons, based on individual degrees of freedom.
Prob. = Probability that the variety mean is not significantly different from the variety listed at the top of the table. For example, a value of 0.050 or less would indicate significance at the 5% level of probability.
Color, establishment and spring greenup were rated once; rust was rated twice and quality seven times.

C. Comparison Description

Plants of new diploid perennial ryegrass 'JS501' differ from plants of the original cross in 1992, perennial ryegrass 'APM' (registered, Reg. No. CV-185, PI 565096) pollinated by perennial ryegrass 'Birdie II' (registered, Reg. No. 133, PI 537452), primarily in the characteristic that only 'JS501' is tolerant to glyphosate-based herbicides.

Plants of new diploid perennial ryegrass 'JS501' look most similar to Top Gun II and 'APM' (registered, Reg. No. CV-185, PI 565096).

'JS501' is further differentiated from 'APM' by having a significantly shorter plant height than 'APM' based on pair-wise comparison (see values in Tables 1 and 7). 'JS501' is also distinguished from 'APM' by its height from ground to flagleaf and inflorescence spike length, where 'JS501' is taller than 'APM' (see values in Tables 1 and 7).

'JS501' is differentiated from Top Gun II by having a significantly longer seed length and wider seed width then Top Gun II (see values in Table 5).

Additional comparisons of 'JS501' are provided in points 1-9 below:

1. Head emergence of 'JS501' was June 12th in Idaho and May 29th in Washington. This was similar to the head emergence of Top Gun II on June 13th in Idaho and May 30th in Washington; head emergency of 'APM' on June 7th in Idaho and May 24th in Washington; and head emergency of 'Linn' on June 5th in Idaho and May 22nd in Washington (Tables 6 and 12).

2. Plant height of 'JS501' is similar to Top Gun II and Linn, but significantly (p=0.05) shorter than 'APM'. Plant height of 'JS501' was 52.2 cm in Idaho and 33.4 cm in Washington.

Plant height of Top Gun II was 50.9 cm in Idaho and 41.6 cm in Washington. Plant height of Linn was 55.8 cm in Idaho and 46.2 cm in Washington. Plant height of 'APM' was 60.8 cm in Idaho and 42.3 cm in Washington (Tables 1 and 7).

3. The height from ground to flagleaf (flagleaf height) of 'JS501' is similar to Top Gun II and Linn but significantly shorter (p=0.05) than 'APM'. Flageleaf height of 'JS501' was 30.6 cm in Idaho and 19.3 cm in Washington. Flageleaf height of Top Gun II was 30.4 cm in Idaho and 25.1 cm in Washington. Flageleaf height of Linn was 30.6 cm in Idaho and 26.8 cm in Washington. Flageleaf height of 'APM' was 38.1 cm in Idaho and 25.6 cm in Washington (Tables 1 and 7).

4. Flagleaf length of 'JS501' is similar to Top Gun II, 'APM', and Linn. Flagleaf length of 'JS501' was 8.2 cm in Idaho and 5.1 cm in Washington. Flagleaf length of Top Gun II was 9.6 cm in Idaho and 7.0 cm in Washington. Flagleaf length of Linn was 9.6 cm in Idaho and 8.2 cm in Washington. Flagleaf length of 'APM' was 9.0 cm in Idaho and 6.2 cm in Washington (Tables 3 and 9).

5. Flagleaf width of 'JS501' is similar to Top Gun II, 'APM', and Linn. Flagleaf width of 'JS501' was at 4.0 mm in Idaho and 3.8 mm in Washington. Flagleaf width of Top Gun II was 3.5 mm in Idaho and 4.0 mm in Washington. Flagleaf width of 'APM''s was 3.4 mm in Idaho and 4.0 mm in Washington. Flagleaf width of Linn was 3.6 mm in Idaho and 4.7 mm in Washington (Tables 3 and 9).

6. 'JS501' has a significantly (p=0.05) shorter inflorescence length than both 'APM' and Linn, but similar to Top Gun II. Spike length of 'JS501' was 12.3 cm in Idaho and 9.2 cm in Washington. Spike length of Top Gun II was 13.1 cm in Idaho and 9.7 cm in Washington. Spike length of 'APM' was 15.7 cm in Idaho and 10.2 cm in Washington. Spike length of Linn was 13.5 cm in Idaho and 12.3 cm in Washington (Tables 1 and 7).

7. The weight of 100 seed of 'JS501' is similar to Top Gun II, 'APM', and Linn. The weight of 100 seed of 'JS501' was 0.1257 g in Idaho and 0.1030 g in Washington. The weight of 100 seed of Top Gun II was 0.1296 g in Idaho and 0.1140 g in Washington. The weight of 100 seed of 'APM' was 0.1258 g in Idaho and 0.1380 g in Washington. The weight of 100 seed of Linn was 0.1900 g in Idaho and 0.1595 g in Washington (Tables 5 and 11).

8. Seed length of 'JS501' is significantly (p=0.05) shorter than 'APM' and Linn, but significantly longer than Top Gun II. Seed length of 'JS501' was 4.88 mm in Idaho and 4.09 mm in Washington. Seed length of Top Gun II was 4.65 mm in Idaho and 3.82 mm in Washington. Seed length of 'APM' was 5.35 mm in Idaho and 4.32 mm in Washington. Seed length of Linn was 5.59 mm in Idaho and 5.1 mm in Washington.

9. Seed width of 'JS501' significantly (p=0.05) thinner than Linn, but significantly wider than 'APM' and Top Gun II. Seed width of 'JS501' was 1.32 mm in Idaho and 1.19 mm in Washington. Seed width of Top Gun II was 1.17 mm in Idaho and 1.11 mm in Washington. Seed width of 'APM' was 1.25 mm in Idaho and 1.15 mm in Washington. Seed width of Linn was 1.39 mm in Idaho and 1.36 mm in Washington (Tables 5 and 11).

A comparison of plants of the glyphosate-tolerant perennial ryegrass known by experimental code BAR Lp 2703 (patented, U.S. Pat. No. 7,465,857) and plants of the new glyphosate-tolerant perennial ryegrass 'JS501' is described in the following Table 16:

TABLE 16

| Trait | New Cultivar 'JS501' | Comparison Cultivar 'BAR Lp 2703' (U.S. Pat. No. 7,465,857) |
|---|---|---|
| Plant Height | 52.2 cm | 67.2 cm |
| Inflorescence Length: | 12.3 cn | 18.0 cn |
| Flag Leaf Height | 30.6 cm | 32.9 cm |
| Flag Leaf Length | 8.2 cm | 9.6 cm |
| Flag Leaf Width | 3.97 mm | 3.0 mm |

Example 4

Genetic Fingerprinting Data of Glyphosate Tolerant Perennial Ryegrass

Molecular markers are widely used to assess genetic variation and relationships among and within a species. The new perennial ryegrass 'JS501' displays tolerance against the broad-spectrum herbicide glyphosate. To understand the molecular basis of the glyphosate tolerance of 'JS501', genetic fingerprinting was completed to determine nucleotide and amino acid sequence of the 5-enolpyruvylshikimate 3-phosphate synthase (EPSPS) gene and its encoded protein respectively. The sequences for the designed primers, as well as, the perennial ryegrass EPSPS gene and protein are provided below.

A. Materials and Methods

RNA was isolated from leaves of the glyphosate tolerant perennial ryegrass (*Lolium perenne*) 'JS501' according to the Trizol method (Invitrogen, Carlsbad, Calif.). First-strand complementary DNA was synthesized with the total RNA (Qiagen) and then used in polymerase chain reactions (PCRs) with primers designed to anneal to transcribed sequences of the gene encoding the glyphosate target EPSPS. Because the EPSPS gene of perennial ryegrass has not yet been sequenced, the sequence of the EPSPS gene of Italian ryegrass (*Lolium multiflorum*) was used as a template for the design of 8 primers, shown as SEQ ID NOS: 1-8 in Table 17 below:

TABLE 17

| SEQ ID NO: | Primer | Primer Sequence (5'-3') |
|---|---|---|
| SEQ ID NO: 1 | JY505 | CAGCCCATCAAGGAGATCTCCGGC |
| SEQ ID NO: 2 | JY506 | CTAGTTCTTCACGAAGGTGCTTAGC |
| SEQ ID NO: 3 | JY507 | CGGCGCCGTGCAGCTGCCCGGCTC |
| SEQ ID NO: 4 | JY508 | AGGTGCTTAGCACGTCAAAGTA |
| SEQ ID NO: 5 | JY509 | GAGCGTTTTGGCGTGACAGCAGAGC |
| SEQ ID NO: 6 | JY510 | CATGTAACCTTCGCTCCCATC |
| SEQ ID NO: 7 | JY511 | GACAGAAGTACAAGTCCCCTGGA |
| SEQ ID NO: 8 | JY512 | CTCCAGTGATTGCAGCACCAGC |

Amplified fragments were isolated from gel agarose after electrophoresis, ligated into high-copy plasmid vectors, and transformed into *E. coli*. Plasmid DNA isolated from the resulting strains was analyzed by restriction digestion and then sequenced. Analysis of the various fragments allowed for determination of the sequence of the perennial ryegrass EPSPS gene and deduction of the encoded protein sequence.

B. Results and Discussion

It has been determined that the glyphosate tolerance of perennial ryegrass 'JS501' is associated with double mutations of the EPSPS gene and its encoded EPSPS protein.

Table 18 below provides a sequence comparison of the EPSPS gene of a wild-type, non-glyphosate tolerant perennial ryegrass (SEQ ID NO:9) to the EPSPS gene of the glyphosate tolerant perennial ryegrass 'JS501' (SEQ ID NO:10) The EPSPS gene of the glyphosate tolerant perennial ryegrass 'JS501' reveals double nucleotide mutations: at position 25, Adenine (A) to Guanine (G); and at position 274, Cytosine (C) to Thymine (T).

TABLE 18

| SEQ ID NO: | Nucleotide Sequence |
| --- | --- |
| SEQ ID NO: 9 (EPSPS Gene of Non Glyphosate Tolerant Wild-Type) | GGCGCCGTGCAGCTGCCCGGCTCCAAGTCGCTCTCCAACCGGATCCTCCTC CTCTCCGCCTTGTCCGAGGGAACAACGGTGGTGGATAACCTGTTGAACAGT GAGGATGTCCACTACATGCTCGAGGCCCTGGACGCGCTCGGCCTCTCCGTG GAAGCAGACAAAGTTGCAAAAAGAGCTGTAGTCGTCGGCTGCGGCGGCAGG TTCCCGATTGAAAAGGATGCCAAGGAGGAAGTAAAGCTCTTCCTGGGGAAC GCTGGAACTGCGATGCGGCCATTGACGGCGGCGGTAGTAGCTGCTGGCGGA AAAGCAACTTATGTTCTTGATGGAGTACCAAGAATGAGGGAGCGACCTATC GGTGACTTAGTTGTCGGTTTGAAACAACTAGGTGCGAATGTTGATTGTTTC CTCGGCACCGACTGCCCACCTGTTCGTATCAACGGCATTGGAGGGCTACCT GGTGGCAAGGTTAAGCTATCTGGTTCCATCAGCAGCCAGTACTTGAGTTCC TTGCTGATGGCTGCTCCTTTGGCTCTTGGGGATGTTGAGATTGAAATCATT GATAAACTAATCTCTGTTCCTTATGTTGAAATGACATTGAGATTGATGGAG CGTTTTGGCGTGACAGCAGAGCATTCTGATAGCTGGGACAGATTCTACATT AAAGGAGGACAGAAGTACAAGTCCCCTGGAAATGCCTATGTCGAAGGTGAT GCCTCAAGTGCGAGCTATTTCTTGGCTGGCGCTGCAATCACTGGAGGAACT GTGACTGTCCAAGGTTGCGGCACCACCAGTTTGCAGGGTGATGTGAAATTT GCTGAGGTACTAGAAATGATGGGAGCGAAAGTTACATGGACCGACACTAGT GTAACTGTTACTGGTCCACCACGTCAGCCCTTTGGAAGGAAACACCTAAAA GCTGTTGATGTCAACATGAACAAAATGCCTGATGTTGCCATGACTCTTGCC GTTGTTGCCCTTTTCGCCGATGGTCCAACTGCTATCAGAGATGTTGCCTCT TGGAGAGTGAAGGAAACCGAGAGAATGGTGGCAATCCGGACGGAACTAACA AAGCTGGGAGCAACGGTAGAGGAAGGCCCAGACTACTGCATTATCACACCA CCAGAGAAGCTGAACGTCACGGCAATCGACACCTACGATGACCACCGGATG GCGATGGCCTTCTCCCTCGCCGCCTGCGCTGAGGTGCCTGTCACGATCAGG GACCCTGGGTGCACCCGCAAGACCTTCCCCAACTACTTTGACGTGCTAAGC ACCT |
| SEQ ID NO: 10 (EPSPS Gene of Glyphosate Tolerant 'JS501') | GGCGCCGTGCAGCTGCCCGGCTCCGAGTCGCTCTCCAACCGGATCCTCCTC CTCTCCGCCTTGTCCGAGGGAACAACGGTGGTGGATAACCTGTTGAACAGT GAGGATGTCCACTACATGCTCGAGGCCCTGGACGCGCTCGGCCTCTCCGTG GAAGCAGACAAAGTTGCAAAAAGAGCTGTAGTCGTCGGCTGCGGCGGCAGG TTCCCGATTGAAAAGGATGCCAAGGAGGAAGTAAAGCTCTTCCTGGGGAAC GCTGGAACTGCGATGCGGTCATTGACGGCGGCGGTAGTAGCTGCTGGCGGA AAAGCAACTTATGTTCTTGATGGAGTACCAAGAATGAGGGAGCGACCTATC GGTGACTTAGTTGTCGGTTTGAAACAACTAGGTGCGAATGTTGATTGTTTC CTCGGCACCGACTGCCCACCTGTTCGTATCAACGGCATTGGAGGGCTACCT GGTGGCAAGGTTAAGCTATCTGGTTCCATCAGCAGCCAGTACTTGAGTTCC TTGCTGATGGCTGCTCCTTTGGCTCTTGGGGATGTTGAGATTGAAATCATT GATAAACTAATCTCTGTTCCTTATGTTGAAATGACATTGAGATTGATGGAG CGTTTTGGCGTGACAGCAGAGCATTCTGATAGCTGGGACAGATTCTACATT AAAGGAGGACAGAAGTACAAGTCCCCTGGAAATGCCTATGTCGAAGGTGAT GCCTCAAGTGCGAGCTATTTCTTGGCTGGCGCTGCAATCACTGGAGGAACT GTGACTGTCCAAGGTTGCGGCACCACCAGTTTGCAGGGTGATGTGAAATTT GCTGAGGTACTAGAAATGATGGGAGCGAAAGTTACATGGACCGACACTAGT GTAACTGTTACTGGTCCACCACGTCAGCCCTTTGGAAGGAAACACCTAAAA GCTGTTGATGTCAACATGAACAAAATGCCTGATGTTGCCATGACTCTTGCC GTTGTTGCCCTTTTCGCCGATGGTCCAACTGCTATCAGAGATGTTGCCTCT TGGAGAGTGAAGGAAACCGAGAGAATGGTGGCAATCCGGACGGAACTAACA AAGCTGGGAGCAACGGTAGAGGAAGGCCCAGACTACTGCATTATCACACCA CCAGAGAAGCTGAACGTCACGGCAATCGACACCTACGATGACCACCGGATG GCGATGGCCTTCTCCCTCGCCGCCTGCGCTGAGGTGCCTGTCACGATCAGG GACCCTGGGTGCACCCGCAAGACCTTCCCCAACTACTTTGACGTGCTAAGC ACCT |

Table 19 below provides a sequence comparison of the reference EPSPS protein from *E. coli* (SEQ ID NO:11) to the EPSPS protein of a wild-type, non-glyphosate tolerant perennial ryegrass (SEQ ID NO:12) and the EPSPS protein of the glyphosate tolerant perennial ryegrass 'JS501' (SEQ ID NO:13).

TABLE 19

| SEQ ID NO: | Amino Acid Sequence |
|---|---|
| SEQ ID NO: 11 (EPSPS Protein from *E. coli*) | MESLTLQPIARVDGTINLPGSKSVSNRALLLAALAHGKTVLTNLLDSDDVRHML NALTALGVSYTLSADRTRCEIIGNGGPLHAEGALELFLGNAGTAMRPLAAALCL GSNDIVLTGEPRMKERPIGHLVDALRLGGAKITYLEQENYPPLRLQGGFTGGNV DVDGSVSSQFLTALLMTAPLAPEDTVIRIKGDLVSKPYIDITLNLMKTFGVEIE NQHYQQFVVKGGQSYQSPGTYLVEGDASSASYFLAAAAIKGGTVKVTGIGRNSM QGDIRFADVLEKMGATICWGDDYISCTRGELNAIDMDMNHIPDAAMTIATAALF AKGTTTLRNIYNWRVKETDRLFAMATELRKVGAEVEEGHDYIRITPPEKLNFAE IATYNDHRMAMCFSLVALSDTPVTILDPKCTAKTFPDYFEQLARISQA |
| SEQ ID NO: 12 (EPSPS Protein of Non-Glyphosate Tolerant Wild-Type Perennial Ryegrass) | GAVQLPGSKSLSNRILLLSALSEGTTVVDNLLNSEDVHYMLEALDALGLSVEAD KVAKRAVVVGCGGRFPIEKDAKEEVKLFLGNAGTAMRPLTAAVVAAGGKATYVL DGVPRMRERPIGDLVVGLKQLGANVDCFLGTDCPPVRINGIGGLPGGKVKLSGS ISSQYLSSLLMAAPLALGDVEIEIIDKLISVPYVEMTLRLMERFGVMAEHSDSW DRFYIKGGQKYKSPGNAYVEGDASSASYFLAGAAITGGTVTVQVAAPPVCRVM |
| SEQ ID NO: 13 (EPSPS Protein of Glyphosate Tolerant Perennial Ryegrass 'JS501') | GAVQLPGSESLSNRILLLSALSEGTTVVDNLLNSEDVHYMLEALDALGLSVEAD KVAKRAVVVGCGGRFPIEKDAKEEVKLFLGNAGTAMRSLTAAVVAAGGKATYVL DGVPRMRERPIGDLVVGLKQLGANVDCFLGTDCPPVRINGIGGLPGGKVKLSGS ISSQYLSSLLMAAPLALGDVEIEIIDKLISVPYVEMTLRLMERFGVMAEHSDSW DRFYIKGGQKYKSPGNAYVEGDASSASYFLAGAAITGGTVTVQGCGTTSLQGDV KFAEVLEMMGAKVT |

SEQ ID NO:12 shows the part of the EPSPS protein of a wild-type, non-glyphosate tolerant perennial ryegrass that is close to the N-terminus and contains conserved amino acids associated with protein function. For instance, the EPSPS protein of a wild-type, non-glyphosate tolerant perennial ryegrass has conserved amino acids: at position 9, Lysine (K), and at position 92, Proline (P). The reference EPSPS protein from *E. coli* (SEQ ID NO:11) has the identical conserved amino acids: at position 22, Lysine (K), and at position 101, Proline (P), whereas the EPSPS protein of the glyphosate tolerant perennial ryegrass 'JS501' (SEQ ID NO:13) reveals double amino acid mutations: at position 9, Lysine (K) to Glutamate (E), and at position 92, Proline (P) to Serine (S).

The double nucleotide mutations of the EPSPS gene of the glyphosate tolerant perennial ryegrass 'JS501' (SEQ ID NO:10) result in the double amino acid mutations in its encoded EPSPS protein (SEQ ID NO:13). The nucleotide mutation at position 274 from Cytosine (C) to Thymine (T) substitutes the amino acid at position 92 from Proline (P) to Serine (S). This mutation was also found in the Salmonella EPSPS-like aroA gene (Stalker et al, *J Biol Chem* 260: 4724-4728, 1985), but has not been identified before in plant EPSPS proteins. The nucleotide mutation at position 25 from Adenine (A) to Guanine (G) substitutes the amino acid at position 22 from Lysine (L) to Glutamate (E). This mutation is present in about 75% of transcripts, and has demonstrated in the past to inactive the EPSPS protein (Huynh et al, *J Biol Chem* 263: 11636-11639, 1988).

Thus, the amino acid substitutions of Glutamate (E) at position 9 and Serine (s) at position 92 of the EPSPS protein of perennial ryegrass confer tolerance to glyphosate.

Example 5

Production of Glyphosate Tolerant Grasses

All of the glyphosate tolerant grass plants of the present invention produced from the following methods, as well as, the progeny or hybrid plants, seed, plant parts, harvested products, tissue cultures of regenerable cells, and protoplasts obtained from the glyphosate tolerant plants of the present invention comprise the isolated perennial ryegrass EPSPS polypeptide of SEQ ID NO:13 of 'JS501'.

The glyphosate tolerant grass plants of the present invention, including 'JS501', can be grown under normal conditions for growing turf-type perennial ryegrasses, and bulk seed for large-scale planting can be obtained by methods known in certified seed production. For example, bulk seed can be produced by planting 'JS501' seeds obtained from ATCC (Accession Number PTA-10370), allowing the mature plants to produce seed by cross-pollination with each other and then collecting the seed. Standard precautions should be taken to prevent cross-pollination from other grasses, such as growing the variety in an isolated plot of sterilized soil, removing adjacent vegetation, etc. 'JS501' seeds deposited with ATCC are breeder seeds; propagation of plants from these seeds can be performed under the conditions specified in the 1998 Oregon Certified Seed Handbook, published by Oregon State University Extension Service, Corvallis, Oreg. 97331.

The glyphosate tolerant grass plants of the present invention, including 'JS501', can be asexually reproduced via vegetative means through the use of tissue culture practices, and can also be produced from offshoots (adventitious buds, tillers) detached from the mother plant and grown in appropriate soil conditions. In addition, asexual propogation of the glyphosate tolerant grass plants of the present invention, including 'JS501', can be performed by detaching rooted stolons and rhizomes from the mother plant and growing identical, daughter plants.

The glyphosate tolerant perennial grass plants of the present invention, can be bred by first sexually crossing a first parental glyphosate tolerant perennial ryegrass 'JS501' plant comprising the EPSPS polypeptide of SEQ ID NO:13 and a second parental non-tolerant glyphosate grass plant that lacks the EPSPS polypeptide of SEQ ID NO:13, thereby producing a plurality of first progeny grass plants; and then selecting a first progeny grass plant that is glyphosate tolerant; and selfing the first progeny grass plants, thereby producing a plurality of second progeny grass plants; and then selecting from the second progeny plants a glyphosate tolerant plant. These steps can further include the back-crossing of the first progeny glyphosate tolerant perennial ryegrass 'JS501' plant or the second progeny glyphosate tolerant grass plant to a second parental grass plant or a third parental grass plant, thereby producing a glyphosate tolerant grass plant.

To confirm maintenance of the glyphosate-tolerance characteristic in produced glyphosate tolerant grass plants of the present invention, including 'JS501', an effective rate of glyphosate herbicide can be applied to the plants and observed for any turf damage. In addition, genetic fingerprinting can be conducted to confirm maintenance of the glyphosate-tolerance characteristic in produced glyphosate tolerant grass plants of the present invention, including 'JS501', as well as, the progeny or hybrid plants, seed, plant parts, harvested products, tissue cultures of regenerable cells, and protoplasts obtained from the glyphosate tolerant plants of the present invention.

Example 6

Exemplary Uses of the Glyphosate Tolerant Perennial Ryegrasses

The glyphosate tolerant grass plants of the present invention, including 'JS501', can be used in the same way as other perennial ryegrass varieties for use on athletic fields, home lawns, golf courses (fairways, roughs and tees), parks, schools, and industrial sites, and forage. However, the tolerance to glyphosate herbicides affords the glyphosate tolerant grass plants of the present invention, including 'JS501', particular advantages over other non-tolerant glyphosate varieties. For example, with current commercially available non-tolerant glyphosate varieties of turf-type perennial ryegrass, the preparation of a lawn that is to be made by seeding requires extensive preparation of the soil to remove weeds that may be present, often including soil fumigation. With the glyphosate tolerant grass plants of the present invention, including 'JS501', such preparation can be avoided since some weeds that begin to grow in the new lawn are readily removed by application of a glyphosate herbicide. With the glyphosate tolerant grass plants of the present invention, including 'JS501', glyphosate herbicides can also be used to remove many of the most troublesome lawn weeds such as crabgrass (*Digitaria sanguinalis*), annual bluegrass (*Poa annua*), rattail fescue (*Vulpia myuros*) and annual ryegrass (*Lolium multiforum*).

Example 7

Introduction of Traits of Glyphosate Tolerant Perennial Ryegrass into Other Varieties The morphological and physiological characteristics, including the glyphosate tolerant trait, of the glyphosate tolerant grass plants of the present invention, including 'JS501', can be introduced into other grass varieties by conventional breeding techniques and molecular techniques.

For example, the glyphosate tolerant perennial ryegrass 'JS501' plants of the present invention can be grown in pollination proximity to another variety of perennial ryegrass, allowing cross-pollination to occur between the glyphosate tolerant variety and the other variety, and then harvesting the hybrid seeds. Plants grown from these hybrid seeds can then be tested for the maintenance of the glyphosate tolerant characteristic accordingly to methods described herein.

The provision of the glyphosate tolerant grass plants of the present invention, including 'JS501', enables the production of glyphosate tolerant progeny and hybrid plants comprising the EPSPS polypeptide of SEQ ID NO:13. Progeny plants are any plants that are the offspring or descendant of any glyphosate tolerant grass plants of the present invention. Progeny plants also include successive generations of the offspring, for example, those plants selected for glyphosate tolerance using the methods described herein. First-generation progeny may retain the glyphosate tolerance characteristic of the glyphosate tolerant grass plant parent. However, if a first-generation progeny does not retain the desired level of glyphosate tolerance observed with the glyphosate tolerant grass plants of the present invention, subsequent generations of offspring can be recycled for glyphosate tolerance which have at least the same glyphosate tolerant characteristic of the glyphosate tolerant grass plants described herein. In another example, subsequent generations of offspring can have a glyphosate tolerance that exceeds that of the glyphosate tolerant grass plants described herein.

In addition, the glyphosate tolerant grass plants of the present invention, including 'JS501', can be used as transformation targets for the production of transformed/transgenic plants. In certain examples, the present disclosure contemplates the transformation of cells derived from the glyphosate tolerant plants of the present invention comprising at least one transgene. Examples of methods of transforming plants are described in U.S. Pat. No. 6,025,545 and Jain and Jain (*Indian J. Exp. Biol.* 38:6-17, 2000) herein incorporated by reference.

Any methods, comprising a technique selected from the group consisting of: asexual reproduction techniques, sexual reproduction techniques, and molecular techniques, and using the glyphosate tolerant perennial ryegrass plant of the present invention, including 'JS501', are part of this invention. Thus, any techniques including, but not limited to, vegetative propagation, selfing, backcrossing, hybrid production, crossing, transforming, tissue culture regeneration, and the like, using the glyphosate tolerant perennial ryegrass plant of the present invention, including 'JS501', are part of this invention.

Further, all non-transgenic and transgenic/transformed plants, produced using the glyphosate tolerant perennial ryegrass of the present invention as a parent are within the scope of this invention, including those plants developed from varieties derived from the glyphosate tolerant perennial ryegrass of the present invention. Also, part of this invention, are the progeny or hybrid plants, seed, plant parts, harvested products, tissue cultures of regenerable cells, and protoplasts obtained from the glyphosate tolerant perennial ryegrass plants of the present invention, including 'JS501'.

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications are herein incorporated by reference to the same extent as if each individual publication or patent application were specifically and individually indicated to be incorporated by reference in its entirety.

What is claimed is:

1. A glyphosate tolerant perennial ryegrass plant named 'JS501,' wherein seed from said plant are deposited with American Type Culture Collection (ATCC) and designated Patent Deposit Designation No.: PTA-10370.

2. A perennial ryegrass seed having American Type Culture Collection (ATCC) Patent Deposit Designation No.: PTA-10370.

3. A 'JS501' plant or plant parts produced from the seed having ATCC Patent Deposit Designation No.: PTA-10370.

4. A harvested product obtained from the glyphosate tolerant perennial ryegrass plant of claim 1, wherein said harvested product has glyphosate tolerance.

5. A method of producing glyphosate tolerant perennial ryegrass progeny or a hybrid thereof comprising the steps of (a) crossing a 'JS501' plant, as either the female or seed parent or male or pollen parent, with a second perennial ryegrass plant, and (b) selecting progeny that are glyphosate tolerant or heterozygous for the genes conferring glyphosate tolerance, wherein seed from said 'JS501' plant are deposited with American Type Culture Collection (ATCC) and designated Patent Deposit Designation No.: PTA-10370.

6. The method according to claim 5, wherein the second perennial ryegrass plant is 'JS501'.

7. A method of producing glyphosate tolerant perennial ryegrass comprising the steps of (a) crossing a 'JS501' plant, as either the female or seed parent or male or pollen parent, with a second perennial ryegrass plant, (b) harvesting seeds produced from said cross, and (c) producing and selecting glyphosate tolerant progeny and progeny that are heterozygous for glyphosate tolerance from said harvested seeds, wherein seed from said 'JS501' plant are deposited with American Type Culture Collection (ATCC) and designated Patent Deposit Designation No.: PTA-10370.

8. The method according to claim 7, wherein the second perennial ryegrass plant is 'JS501'.

9. A method of producing glyphosate tolerant perennial ryegrasses, comprising the steps of (a) selfing 'JS501', and (b) selecting glyphosate tolerant progeny and progeny that are heterozygous for glyphosate tolerance, wherein seed from said 'JS501' plant are deposited with American Type Culture Collection (ATCC) and designated Patent Deposit Designation No.: PTA-10370.

10. The harvested product of claim 4, wherein said product is selected from the group consisting of seed blends and mixtures; turfgrass sprigs, plugs and sod; and fodder blends and mixtures.

* * * * *

UNITED STATES PATENT AND TRADEMARK OFFICE
CERTIFICATE OF CORRECTION

PATENT NO. : 8,604,279 B2
APPLICATION NO. : 12/906738
DATED : December 10, 2013
INVENTOR(S) : Brede et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 296 days.

Signed and Sealed this
Twenty-first Day of July, 2015

Michelle K. Lee
*Director of the United States Patent and Trademark Office*